US011241196B2

(12) United States Patent
Linder et al.

(10) Patent No.: US 11,241,196 B2
(45) Date of Patent: Feb. 8, 2022

(54) SIGNAL CONDUCTING DEVICE FOR CONCURRENT POWER AND DATA TRANSFER TO AND FROM UN-WIRED SENSORS ATTACHED TO A MEDICAL DEVICE

(71) Applicant: XENTER, INC., Salt Lake City, UT (US)

(72) Inventors: Richard J. Linder, Sandy, UT (US); Edwin Meade Maynard, Salt Lake City, UT (US); Scott Kenneth Marland, Bountiful, UT (US); Cory Rex Estes, Mapleton, UT (US)

(73) Assignee: XENTER, INC., Salt Lake City, UT (US)

( * ) Notice: Subject to any disclaimer, the term of this patent is extended or adjusted under 35 U.S.C. 154(b) by 0 days.

(21) Appl. No.: 17/205,614

(22) Filed: Mar. 18, 2021

(65) Prior Publication Data

US 2021/0290059 A1 Sep. 23, 2021

Related U.S. Application Data

(60) Provisional application No. 63/044,960, filed on Jun. 26, 2020, provisional application No. 62/992,695, filed on Mar. 20, 2020.

(51) Int. Cl.
*A61B 5/00* (2006.01)
*A61B 5/0215* (2006.01)
(Continued)

(52) U.S. Cl.
CPC .......... *A61B 5/6852* (2013.01); *A61B 5/0002* (2013.01); *A61B 5/0215* (2013.01);
(Continued)

(58) Field of Classification Search
CPC ... A61B 5/0002; A61B 5/6852; A61B 5/0059; A61B 2503/40; A61B 2560/0214
See application file for complete search history.

(56) References Cited

U.S. PATENT DOCUMENTS

| 4,595,012 A | 6/1986 | Webler et al. |
| 4,827,941 A | 5/1989 | Taylor et al. |

(Continued)

FOREIGN PATENT DOCUMENTS

| CN | 103720463 A | 4/2014 |
| CN | 105919559 | 9/2016 |

(Continued)

OTHER PUBLICATIONS

Aldaoud, et al. "A stent-based power and data link for sensing intravascular biological indicators." IEEE Sensors Letters 2.4 (2018): 1-4.

(Continued)

*Primary Examiner* — Lindsey G Wehrheim
(74) *Attorney, Agent, or Firm* — Workman Nydegger

(57) ABSTRACT

A medical device system for concurrent power and data transfer comprises an elongated conductive member. At least a portion of the elongated conductive member is configured for insertion within an intraluminal space. One or more sensors that are in electrical connection with the elongated conductive member. The medical device system uniquely allocates each of the plurality of unique contiguous segments within a signal space to one of (i) one or more power channels or (ii) one or more signal channels. The medical device system then sends the electrical signals, via the elongated conductive member, to one or more sensors that are in electrical connection with the elongated conductive member. The medical device harvests energy from the electrical signals. The medical device system isolates transmitted data signals within at least one of the one or more (Continued)

signal channels the data signals generated by the one or more sensors.

24 Claims, 13 Drawing Sheets

(51) Int. Cl.
| | |
|---|---|
| *A61M 25/09* | (2006.01) |
| *H02J 50/90* | (2016.01) |
| *H02J 50/05* | (2016.01) |
| *H02J 50/40* | (2016.01) |
| *A61B 5/07* | (2006.01) |
| *A61B 1/05* | (2006.01) |
| *A61M 25/01* | (2006.01) |
| *A61B 8/12* | (2006.01) |

(52) U.S. Cl.
CPC ............ *A61B 5/02158* (2013.01); *A61B 5/07* (2013.01); *A61B 5/6851* (2013.01); *A61M 25/09* (2013.01); *H02J 50/05* (2016.02); *H02J 50/402* (2020.01); *H02J 50/90* (2016.02); *A61B 1/05* (2013.01); *A61B 5/0059* (2013.01); *A61B 8/12* (2013.01); *A61B 2503/40* (2013.01); *A61B 2560/0214* (2013.01); *A61B 2560/0219* (2013.01); *A61B 2562/0247* (2013.01); *A61B 2562/06* (2013.01); *A61B 2562/222* (2013.01); *A61M 2025/0183* (2013.01)

(56) References Cited

U.S. PATENT DOCUMENTS

| | | | |
|---|---|---|---|
| 4,850,358 | A | 7/1989 | Millar |
| 4,917,104 | A | 4/1990 | Rebell |
| 5,154,725 | A | 10/1992 | Leopold |
| 5,366,490 | A | 11/1994 | Edwards et al. |
| 5,368,035 | A | 11/1994 | Hamm et al. |
| 5,564,434 | A | 10/1996 | Halperin et al. |
| 5,651,767 | A | 7/1997 | Schulman et al. |
| 5,790,081 | A | 8/1998 | Unwin |
| 5,814,089 | A | 9/1998 | Stokes et al. |
| 5,860,974 | A | 1/1999 | Abele |
| 6,004,269 | A | 12/1999 | Crowley et al. |
| 6,167,763 | B1 | 1/2001 | Tenerz et al. |
| 6,211,799 | B1 | 4/2001 | Post et al. |
| 6,245,020 | B1 | 6/2001 | Moore et al. |
| 6,248,076 | B1 | 6/2001 | White et al. |
| 6,479,785 | B1 | 11/2002 | Fugo et al. |
| 6,728,571 | B1 | 4/2004 | Barbato |
| 7,210,940 | B2 | 5/2007 | Baily et al. |
| 7,645,233 | B2 | 1/2010 | Tulkki et al. |
| 7,651,578 | B2 | 1/2010 | Sharrow et al. |
| 8,076,821 | B2 | 12/2011 | Degertekin |
| 8,277,386 | B2 | 10/2012 | Ahmed et al. |
| 8,362,673 | B2 | 1/2013 | Hsu |
| 8,473,067 | B2 | 6/2013 | Hastings et al. |
| 8,478,384 | B2 | 7/2013 | Schmitt et al. |
| 8,882,763 | B2 | 11/2014 | Stevenson et al. |
| 9,106,270 | B2 | 8/2015 | Puterbaugh et al. |
| 9,192,306 | B2 | 11/2015 | Chen |
| 9,259,206 | B2 | 2/2016 | Degertekin et al. |
| 9,486,355 | B2 | 11/2016 | Gustus et al. |
| 9,667,323 | B2 | 5/2017 | Habraken et al. |
| 9,675,325 | B2 | 6/2017 | Moore et al. |
| 10,028,667 | B2 | 7/2018 | Kishida et al. |
| 10,080,872 | B2 | 9/2018 | Webler |
| 10,390,791 | B2 | 8/2019 | Courtney et al. |
| 10,391,292 | B2 | 8/2019 | Sutton |
| 10,418,755 | B2 | 9/2019 | Kahlman |
| 10,463,259 | B2 | 11/2019 | Glover et al. |
| 10,463,274 | B2 | 11/2019 | Kassab et al. |
| 10,531,841 | B2 | 1/2020 | Merritt et al. |
| 10,569,072 | B2 | 2/2020 | Agrawal et al. |
| 10,737,086 | B2 | 8/2020 | Agrawal et al. |
| 10,765,853 | B2 | 9/2020 | Neff et al. |
| 10,842,981 | B2 | 11/2020 | Agrawal et al. |
| 10,869,603 | B2 | 12/2020 | Millett et al. |
| 10,881,846 | B2 | 1/2021 | Furnish et al. |
| 2001/0001317 | A1 | 5/2001 | Duerig et al. |
| 2001/0029337 | A1 | 10/2001 | Pantages et al. |
| 2002/0013527 | A1 | 1/2002 | Hoek et al. |
| 2002/0151823 | A1 | 10/2002 | Miyata et al. |
| 2003/0083723 | A1 | 5/2003 | Wilkinson et al. |
| 2003/0120271 | A1 | 6/2003 | Burnside et al. |
| 2004/0064024 | A1 | 4/2004 | Sommer |
| 2005/0143664 | A1 | 6/2005 | Chen et al. |
| 2006/0009817 | A1 | 1/2006 | Tulkki |
| 2006/0264925 | A1 | 11/2006 | Sharareh et al. |
| 2007/0118035 | A1 | 5/2007 | Secora |
| 2007/0191830 | A1 | 8/2007 | Crompton et al. |
| 2007/0255166 | A1 | 11/2007 | Carney et al. |
| 2008/0021336 | A1 | 1/2008 | Dobak, III |
| 2008/0177183 | A1 | 7/2008 | Courtney et al. |
| 2009/0005859 | A1 | 1/2009 | Keilman |
| 2009/0110148 | A1* | 4/2009 | Zhang ............... A61B 6/04 378/95 |
| 2009/0156926 | A1 | 6/2009 | Messerly et al. |
| 2009/0171345 | A1 | 7/2009 | Miller et al. |
| 2009/0259772 | A1 | 10/2009 | Ketko et al. |
| 2009/0284332 | A1 | 11/2009 | Moore et al. |
| 2010/0087143 | A1 | 4/2010 | Bonin |
| 2010/0113939 | A1 | 5/2010 | Mashimo et al. |
| 2011/0190756 | A1 | 8/2011 | Venkatachalam et al. |
| 2011/0270369 | A1 | 11/2011 | Tekmen et al. |
| 2012/0209061 | A1 | 8/2012 | Kato |
| 2013/0064043 | A1 | 3/2013 | Degertekin et al. |
| 2013/0109980 | A1 | 5/2013 | Teo |
| 2013/0123638 | A1 | 5/2013 | Tom et al. |
| 2013/0204111 | A1 | 8/2013 | Flanders |
| 2013/0289424 | A1 | 10/2013 | Brockway et al. |
| 2013/0296692 | A1 | 11/2013 | Vanney et al. |
| 2014/0066705 | A1 | 3/2014 | Robertson et al. |
| 2014/0171788 | A1 | 6/2014 | Stigall |
| 2014/0180031 | A1 | 6/2014 | Anderson |
| 2014/0187978 | A1 | 7/2014 | Millett et al. |
| 2014/0236017 | A1 | 8/2014 | Degertekin et al. |
| 2014/0248801 | A1 | 9/2014 | Riezebos et al. |
| 2014/0323860 | A1 | 10/2014 | Courtney et al. |
| 2015/0141854 | A1 | 5/2015 | Eberle et al. |
| 2015/0208901 | A1 | 7/2015 | Gazdzinski |
| 2015/0216403 | A1 | 8/2015 | Whitmore, III |
| 2015/0305708 | A1 | 10/2015 | Stigall et al. |
| 2015/0313478 | A1 | 11/2015 | Veszelei et al. |
| 2016/0249817 | A1 | 9/2016 | Mazar et al. |
| 2016/0310020 | A1 | 10/2016 | Warnking et al. |
| 2017/0136496 | A1 | 5/2017 | Jacobs et al. |
| 2017/0164867 | A1 | 6/2017 | Kassab et al. |
| 2017/0164925 | A1 | 6/2017 | Marshall et al. |
| 2017/0215801 | A1 | 8/2017 | Jung et al. |
| 2017/0266433 | A1 | 9/2017 | Daniels et al. |
| 2018/0125365 | A1 | 5/2018 | Hunter et al. |
| 2018/0262236 | A1 | 9/2018 | Kahlman |
| 2018/0263515 | A1 | 9/2018 | Raval |
| 2019/0053787 | A1 | 2/2019 | Stigall et al. |
| 2019/0070402 | A1 | 3/2019 | Isaacson |
| 2019/0133462 | A1 | 5/2019 | Millett et al. |
| 2019/0167351 | A1 | 6/2019 | Salazar et al. |
| 2019/0184159 | A1 | 6/2019 | Yeh et al. |
| 2019/0290139 | A1 | 9/2019 | Sio et al. |
| 2019/0358387 | A1 | 11/2019 | Elbadry et al. |
| 2019/0380651 | A1 | 12/2019 | Carreel et al. |
| 2020/0022587 | A1 | 1/2020 | Glover et al. |
| 2020/0054227 | A1 | 2/2020 | Van Rens |
| 2021/0290100 | A1 | 9/2021 | Linder et al. |

(56) References Cited

U.S. PATENT DOCUMENTS

2021/0290164 A1  9/2021  Linder et al.
2021/0290198 A1  9/2021  Linder et al.

FOREIGN PATENT DOCUMENTS

| DE | 19621003 | | 1/1997 |
|---|---|---|---|
| JP | 2016-518870 | A | 3/2017 |
| WO | 2018/017547 | | 1/2018 |
| WO | 2020/030776 | A1 | 2/2020 |

OTHER PUBLICATIONS

Degertekin FL, Guldiken RO, Karaman M. Annular-ring CMUT arrays for forward-looking IVUS: transducer characterization and imaging. IEEE Trans Ultrason Ferroelectr Freq Control. Feb. 2006;53(2):474-82.

E. F. Arkan and F. L. Degertekin, "Analysis and Design of High-Frequency 1-D CMUT Imaging Arrays in Noncollapsed Mode," in IEEE Transactions on Ultrasonics, Ferroelectrics, and Frequency Control, vol. 66, No. 2, pp. 382-393, Feb. 2019.

G. Jung, C. Tekes, A. Pirouz, F. L. Degertekin and M. Ghovanloo, "Supply-Doubled Pulse-Shaping High Voltage Pulser for CMUT Arrays," in IEEE Transactions on Circuits and Systems II: Express Briefs, vol. 65, No. 3, pp. 306-310, Mar. 2018.

Gurun G, Hasler P, Degertekin F. Front-end receiver electronics for high-frequency monolithic CMUT-on-CMOS imaging arrays. IEEE Transactions on Ultrasonics, Ferroelectrics, and Frequency Control. Aug. 2011;58(8):1658-1668.

Gurun G, Tekes C, Zahorian J, Xu T, Satir S, Karaman M, Hasler J, Degertekin FL. Single-chip CMUT-on-CMOS front-end system for real-time volumetric IVUS and ICE imaging. IEEE Trans Ultrason Ferroelectr Freq Control. Feb. 2014;61(2):239-50.

J. Lim, C. Tekes, E. F. Arkan, A. Rezvanitabar, F. L. Degertekin and M. Ghovanloo, "Highly Integrated Guidewire Ultrasound Imaging System-on-a-Chip," in IEEE Journal of Solid-State Circuits, vol. 55, No. 5, pp. 1310-1323, May 2020.

J. Lim, C. Tekes, F. L. Degertekin and M. Ghovanloo, "Towards a Reduced-Wire Interface for CMUT-Based Intravascular Ultrasound Imaging Systems," in IEEE Transactions on Biomedical Circuits and Systems, vol. 11, No. 2, pp. 400-410, Apr. 2017.

J. Zahorian et al., "Monolithic CMUT-on-CMOS Integration for Intravascular Ultrasound Applications," in IEEE Transactions on Ultrasonics, Ferroelectrics, and Frequency Control, vol. 58, No. 12, pp. 2659-2667, Dec. 2011.

Lim J, Arkan EF, Degertekin FL, Ghovanloo M. Toward a reduced-wire readout system for ultrasound imaging. Annu Int Conf IEEE Eng Med Biol Soc. 2014;2014:5080-4.

Lim J, Rezvanitabar A, Degertekin FL, Ghovanloo M. An Impulse Radio PWM-Based Wireless Data Acquisition Sensor Interface. IEEE Sens J. Jan. 15, 2019;19(2):603-614.

Lu, et al. "A review on the recent development of capacitive wireless power transfer technology." Energies 10.11 (2017): 1752.

Pirouz, A.; Degertekin, F.L. An Analysis Method for Capacitive Micromachined Ultrasound Transducer (CMUT) Energy Conversion during Large Signal Operation. Sensors 2019, 19, 876.

S. Satir and F. L. Degertekin, "A nonlinear lumped model for ultrasound systems using CMUT arrays," in IEEE Transactions on Ultrasonics, Ferroelectrics, and Frequency Control, vol. 62, No. 10, pp. 1865-1879, Oct. 2015.

S. Satir, J. Zahorian and F. L. Degertekin, "A large-signal model for CMUT arrays with arbitrary membrane geometry operating in non-collapsed mode," in IEEE Transactions on Ultrasonics, Ferroelectrics, and Frequency Control, vol. 60, No. 11, pp. 2426-2439, Nov. 2013.

Satir S, Degertekin FL. Phase and Amplitude Modulation Methods for Nonlinear Ultrasound Imaging With CMUTs. IEEE Trans Ultrason Ferroelectr Freq Control Aug. 2016;63(8):1086-92.

Sharei, et al. "Data communication pathway for sensing guidewire at proximal side: A review." Journal of Medical Devices 11.2 (2017).

Tanase et al. "Multi-parameter sensor system with intravascular navigation for catheter/guide wire application", Sensors and Actuators A: Physical vols. 97-98, Apr. 1, 2002, pp. 116-124.

Tekes C, Zahorian J, Gurun G, et al. Volumetric imaging using single chip integrated CMUT-on-CMOS IVUS array. Annu Int Conf IEEE Eng Med Biol Soc. 2012;2012:3195-3198.

Non-Final Rejection dated May 24, 2021 for U.S. Appl. No. 17/205,964.

Final Office Action received for U.S. Appl. No. 17/205,754, dated Aug. 25, 2021, 12 pages.

Final Office Action received for U.S. Appl. No. 17/205,854, dated Sep. 23, 2021, 14 pages.

International Search Report and Written Opinion received for PCT Patent Application No. PCT/US21/023198, dated Jun. 14, 2021, 2 pages.

International Search Report and Written Opinion received for PCT Patent Application No. PCT/US21/23135, dated Jun. 8, 2021, 8 pages.

International Search Report and Written Opinion received for PCT Patent Application No. PCT/US21/23148, dated Jun. 4, 2021, 7 pages.

International Search Report and Written Opinion received for PCT Patent Application No. PCT/US21/23184, dated Jun. 7, 2021, 10 pages.

* cited by examiner

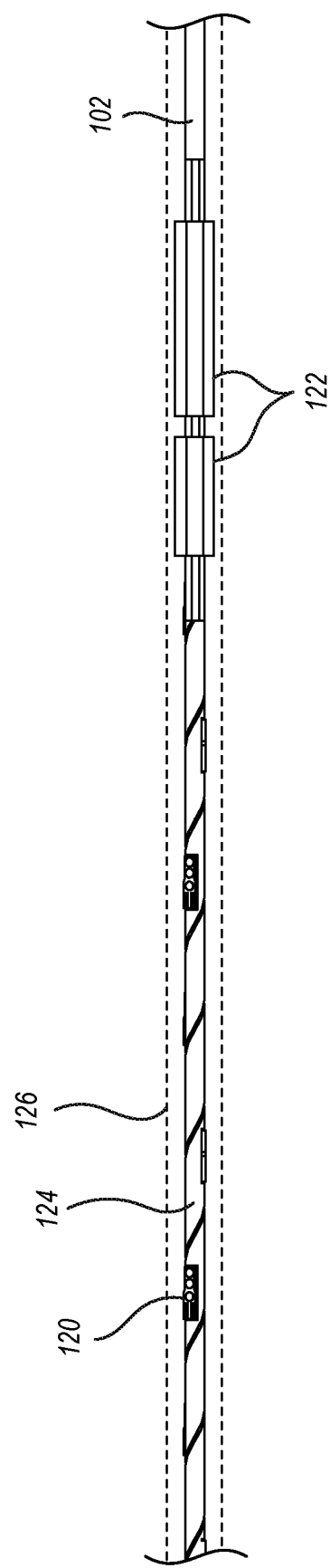

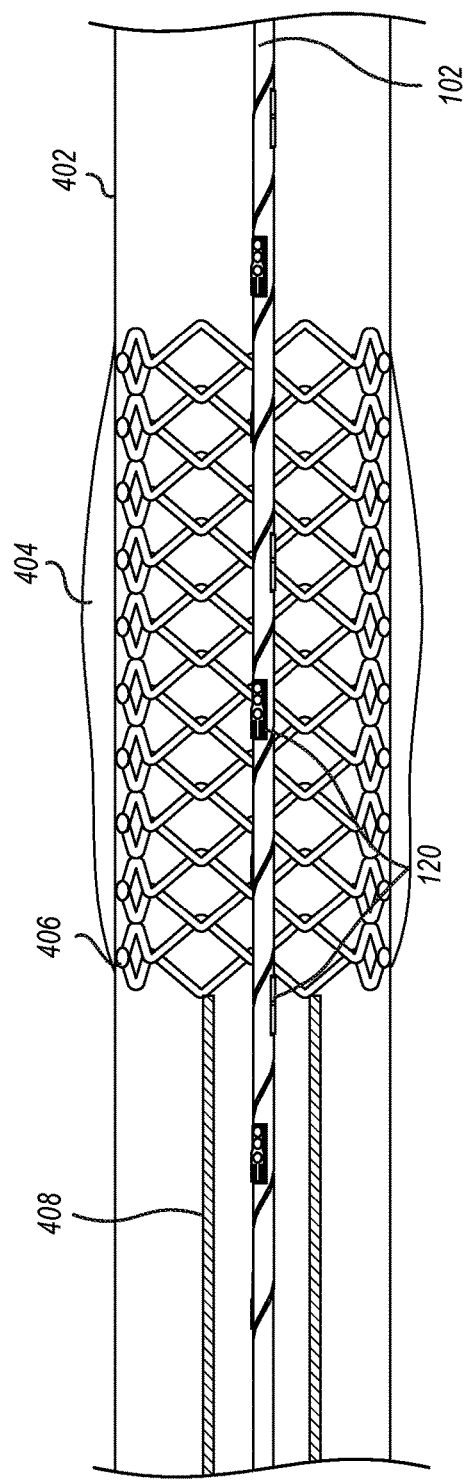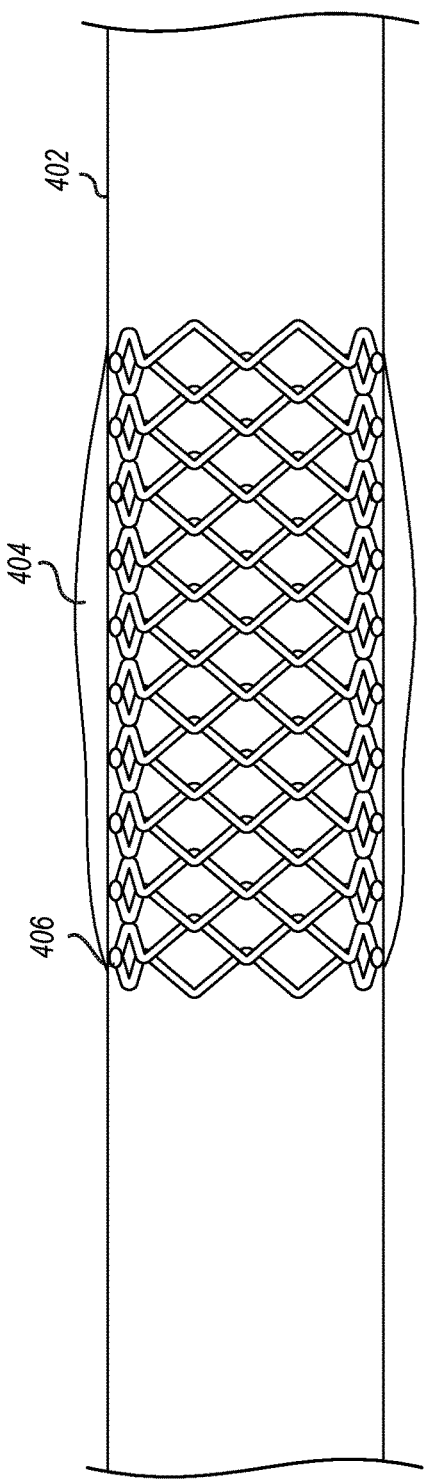
FIG. 4C
FIG. 4D

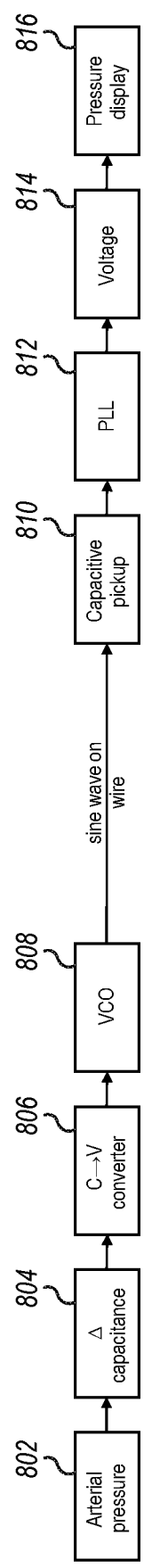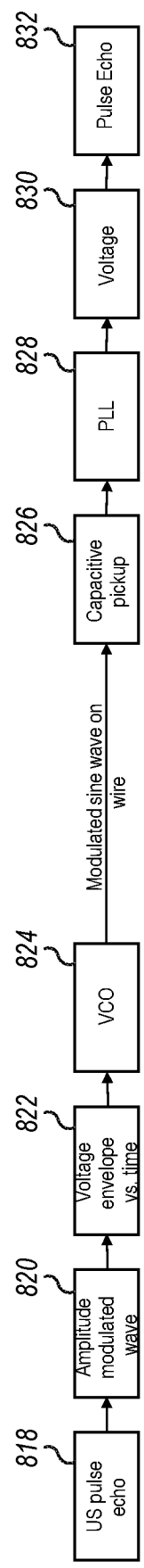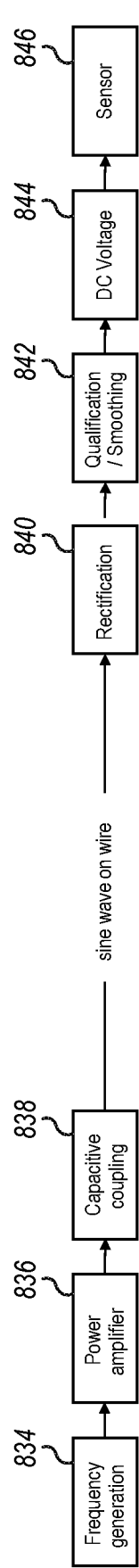
FIG. 8A
FIG. 8B
FIG. 8C

SIGNAL CONDUCTING DEVICE FOR CONCURRENT POWER AND DATA TRANSFER TO AND FROM UN-WIRED SENSORS ATTACHED TO A MEDICAL DEVICE

CROSS-REFERENCE TO RELATED APPLICATIONS

This application claims priority to U.S. Provisional Patent Application Ser. No. 62/992,695, filed Mar. 20, 2020 and titled "CATHETER SYSTEM, DEVICE, AND METHOD THEREOF," and to U.S. Provisional Patent Application Ser. No. 63/044,960, filed Jun. 26, 2020 and titled "CATHETER AND GUIDEWIRE SYSTEMS WITH ENHANCED LOCATION AND CHARACTERIZATION FEATURES." The entire contents of each of the above applications is incorporated herein by reference in their entireties.

Additionally, the present application is related to U.S. patent application Ser. No. 17/205,754 filed Mar. 18, 2021 entitled "OPERATIVELY COUPLED DATA AND POWER TRANSFER DEVICE FOR MEDICAL GUIDEWIRES AND CATHETERS WITH SENSORS", U.S. patent application Ser. No. 17/205,854 filed Mar. 18, 2021 entitled CATHETER FOR IMAGING AND MEASUREMENT OF PRESSURE AND OTHER PHYSIOLOGICAL PARAMETERS", and U.S. patent application Ser. No. 17/205,964 filed Mar. 18, 2021 entitled "GUIDEWIRE FOR IMAGING AND MEASUREMENT OF PRESSURE AND OTHER PHYSIOLOGICAL PARAMETERS". The entire contents of each of the above applications is incorporated herein by reference in their entireties.

BACKGROUND

The present invention relates generally to medical devices, including intraluminal devices such as guidewires and catheters that include various sensors for simultaneous and/or continuous measuring of one or more physiological parameters.

Guidewire devices are often used to lead or guide catheters or other interventional devices to a targeted anatomical location within a patient's body. Typically, guidewires are passed into and through a patient's vasculature in order to reach the target location, which may be at or near the patient's heart or brain, for example. Radiographic imaging is typically utilized to assist in navigating a guidewire to the targeted location. Guidewires are available with various outer diameter sizes. Widely utilized sizes include 0.010, 0.014, 0.016, 0.018, 0.024, and 0.035 inches in diameter, for example, though they may also be smaller or larger in diameter.

In many instances, a guidewire is placed within the body during the interventional procedure where it can be used to guide multiple catheters or other interventional devices to the targeted anatomical location. Once in place, a catheter can be used to aspirate clots or other occlusions, or to deliver drugs, stents, embolic devices, radiopaque dyes, or other devices or substances for treating the patient.

These types of interventional devices can include sensors located at the distal portion in order to provide added functionality to the device. For example, intravascular ultrasound (IVUS) is an imaging technique that utilizes a catheter with an ultrasound imaging sensor attached to the distal portion. Ultrasound is utilized to image within targeted vasculature (typically the coronary arteries).

The use of such sensors introduces several challenges. In particular, the interventional devices involved have very limited space to work in, given the stringent dimensional constraints involved. Moreover, integrating the sensors with the interventional device in a way that maintains effective functionality can be challenging.

Another issue common to the field is proper localization and positioning of the distal portion of the device at the target location. If the device tip is improperly positioned during insertion, or if the tip migrates away from the desired position after insertion, various risks can arise. For catheter implementations, for example, improper positioning can lead to fluid infusions that can cause pain or injury to the patient, increased thrombosis rates, delays in therapy, device breakage or malfunction, delays due to device replacement, and additional costs associated with the device replacement and the additional time required by the attending physician and the medical center.

Further, conventional approaches to internal imaging and catheter localization require the injection of dye and/or the use of X-rays. Each of these can be harmful to the subject. In addition, such imaging radiation can be harmful to the physicians and staff exposed to the radiation.

The use of such interventional devices is also challenging due to the need to manage several long lengths of wires and other components, including guidewires, power cables, data wires, and the like. Care must be taken with respect to what is allowed in the sterile field and when it can be removed. Additional staff is often required simply to manage such wires and cables.

As such, there is an ongoing need for improved interventional devices that effectively integrate sensors, effectively manage power and data communication with the sensors, effectively communicate data off of the device for additional processing and enable more effective positioning of the medical device in the desired target position within the vasculature or other targeted anatomy.

SUMMARY

Disclosed embodiments include a method for concurrent power and data transfer in a medical device. The method comprises providing an elongated conductive member, at least a portion thereof configured for insertion within an intraluminal space. The elongated conductive member comprises a proximal portion and a distal portion configured to conduct electrical signals. The method also includes allocating a signal space into a plurality of unique contiguous segments. Additionally, the method includes uniquely allocating each of the plurality of unique contiguous segments to one of (i) one or more power channels or (ii) one or more signal channels. In addition, the method includes sending the electrical signals, via the elongated conductive member, to one or more sensors that are in electrical connection with the elongated conductive member. Further, the method includes harvesting energy from the electrical signals within at least one of the one or more power channels. Further still, the method includes isolating transmitted data signals from at least one of the one or more signal channels, the data signals transmitted via the elongated conductive member and the data signals generated by the one or more sensors.

Additional disclosed embodiments include a medical device system for concurrent power and data transfer. The medical device system comprises an elongated conductive member, at least a portion thereof configured for insertion within an intraluminal space. The elongated conductive member comprises a proximal portion and a distal portion.

The medical device system also comprises one or more sensors that are in electrical connection with the elongated conductive member. Additionally, the medical device system comprises one or more electrical components that are physically configured such that, when activated, the one or more electrical components cause the medical device system to perform various acts. For example, the medical device system allocates a signal space into a plurality of unique contiguous segments. Additionally, the medical device system uniquely allocates each of the plurality of unique contiguous segments to one of (i) one or more power channels or (ii) one or more signal channels. The medical device system also sends the electrical signals, via the elongated conductive member, to one or more sensors that are in electrical connection with the elongated conductive member. Further, the medical device system harvests energy from the electrical signals within at least one of the one or more power channels. Further still, the medical device system isolates transmitted data signals within at least one of the one or more signal channels, via the elongated conductive member, the data signals generated by the one or more sensors.

Further disclosed embodiments include a computer-readable media comprising one or more physical computer-readable storage media having stored thereon computer-executable instructions that, when executed at one or more processors, cause a computer system to perform a method for concurrent power and data transfer in a single-member medical device. The method comprises providing an elongated conductive member, at least a portion thereof configured for insertion within an intraluminal space. The elongated conductive member comprises a proximal portion and a distal portion configured to conduct electrical signals. The method also includes allocating a signal space into a plurality of unique contiguous segments. Additionally, the method includes uniquely allocating each of the plurality of unique contiguous segments to one of (i) one or more power channels or (ii) one or more signal channels. In addition, the method includes sending the electrical signals, via the elongated conductive member, to one or more sensors that are in electrical connection with the elongated conductive member. Further, the method includes harvesting energy from the electrical signals within at least one of the one or more power channels. Further still, the method includes isolating transmitted data signals from at least one of the one or more signal channels, the data signals transmitted via the elongated conductive member and the data signals generated by the one or more sensors.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

FIG. 3B is an expanded view of a distal section of the guidewire to better illustrate exemplary sensor arrangement on the guidewire;

FIGS. 4A-4D illustrate an exemplary use of the guidewire system to effectively guide positioning and deployment of a stent at a targeted stenosis;

FIGS. 8A-8C depict various signal schematic diagrams of the medical device.

DETAILED DESCRIPTION

Overview of Intraluminal Systems

Figure 1:
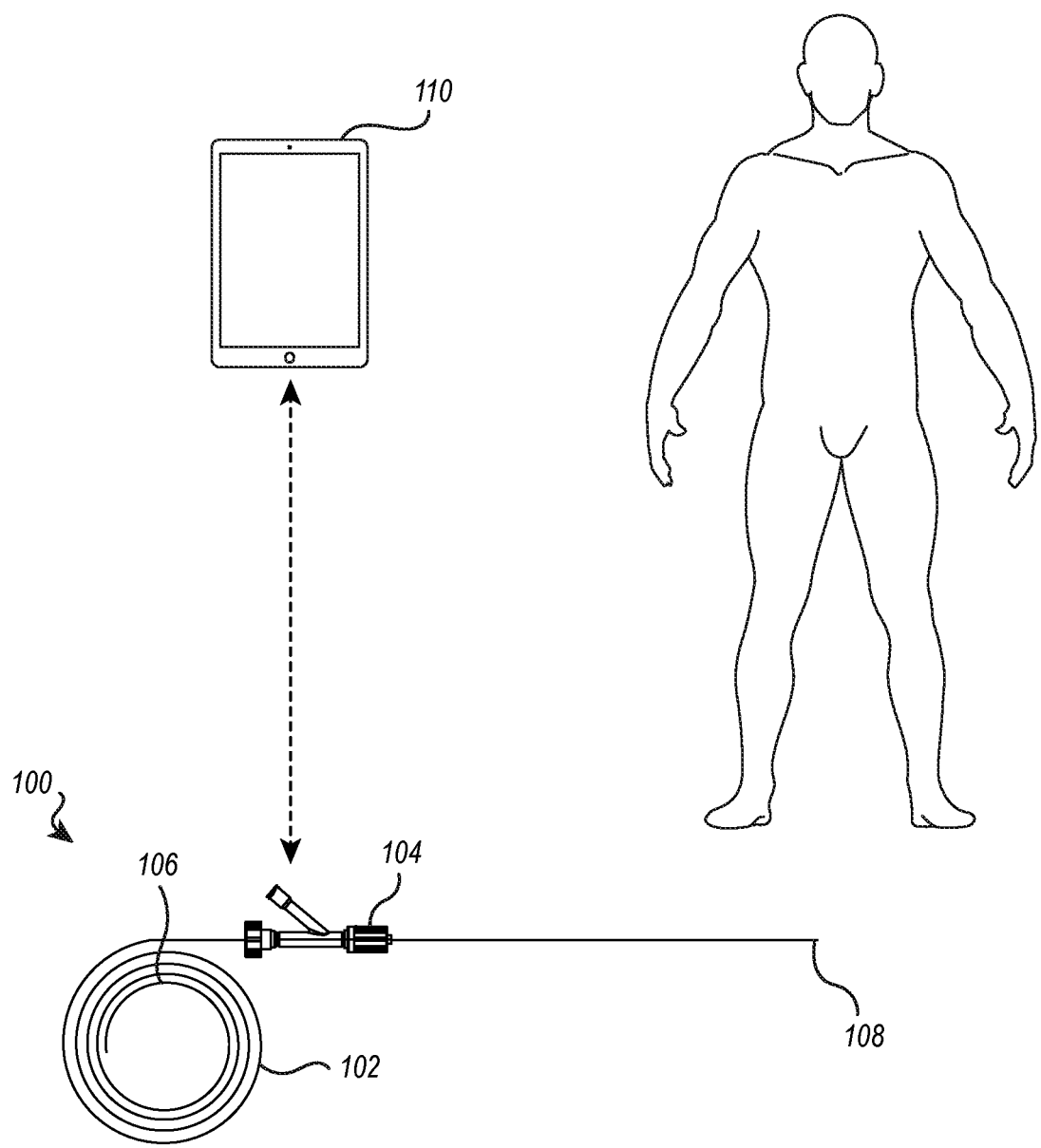
FIG. 1 illustrates a schematic overview of a guidewire system configured to provide one or more of the features described herein.

FIG. 1 illustrates a schematic overview of a guidewire system 100 that may incorporate one or more of the features described herein. The guidewire system 100 includes a wire 102 that is routable through a proximal device 104. The guidewire system 100 may sometimes be alternatively referred to herein as the "guidewire device". As used herein, the wire 102 may also be referred to as a type of elongated conductive member.

As used herein, the elongated conductive member comprises any conductive component that is longer than it is wide. For example, the elongated conductive member includes the wire 102. For the sake of example and explanation, the elongated conductive member may also be referred to as the wire 102; however, one will appreciate the wire 102 is a subset of possible elongated conductive members. For example, the elongated conductive member may also comprise a catheter.

The "wire" of the guidewire system 100 refers to the solid wire element that forms the backbone of the guidewire system 100. The term "wire", when used in the context of the guidewire system 100, is therefore intended to refer to a structure that has sufficient characteristics of torqueability, pushability, and stiffness/flexibility to be navigable within a body (e.g., capable of being positioned within an intraluminal space such as the vasculature). Such a "wire" element is sometimes referred to in the art as a "core", "core wire", or the like. This type of "wire" is therefore intended to be distinguished from smaller, less structured elements such as traces or leads that are capable of carrying an electrical signal but lack sufficient structure to be effectively navigated and positioned within the body to reach targeted anatomy. As an example, a "wire" suitable for use as part of the guidewire system 100 can have an average outside diameter of at least about 0.003 inches, or about 0.005 inches, or about 0.008 inches, or about 0.010 inches. In another example, a "wire" suitable for use as part of the guidewire system 100 can have yield strength above 10 ksi, or more preferably above 30 ksi, or more preferably above 50 ksi, or more preferably above 100 ksi, or more preferably above 150 ksi, or more preferably above 200 ksi, or more preferably above 250 ksi, such as 300 ksi. Additionally, or alternatively, the "wire" suitable for use as part of the guidewire system 100 can have a shear modulus above 6.7 msi, or more preferably above 8 msi, or more preferably above 10 msi, such as about 12 msi. Additionally, or alternatively, the "wire" suitable for use as part of the guidewire system 100 can have a modulus of elasticity of above 16 msi, or more preferably above 20 msi, or more preferably above 25 msi, such as about 30 msi.

The wire 102 of the guidewire system 100 is configured for insertion into the body of a subject. The subject is typically a human, but in other implementations may be a non-human mammal or even non-mammalian animal. Any suitable route of administration may be utilized, depending on particular preferences and/or application needs. Common routes include femoral, radial, and jugular, but the guidewire system 100 may utilized other access routes as needed.

Although many of the examples described herein relate to use of the guidewire system 100 or the catheter system 200 (see FIG. 2) in relation to intravascular procedures (e.g., cardiovascular or neurovascular), it will be understood that the described systems may be utilized in other medical applications as well. Other medical applications where the systems described herein may be utilized include, for example, applications involving access of the lymphatic, urinary/renal, gastrointestinal, reproductive, hepatic, or respiratory systems.

The proximal device 104 is shown here as a hemostatic valve, though in other embodiments the proximal device 104 may include additional or alternative forms. The proximal device 104 may also be referred to herein as the "power and data coupling device 104" or simply the "coupling device 104".

The wire 102 has a proximal portion 106 and a distal portion 108. The length of the wire 102 may vary according to particular application needs and targeted anatomical area. As an example, the wire 102 may have an overall length from proximal portion 106 to distal portion 108 of about 50 cm to about 350 cm, more commonly about 200 cm, depending on particular application needs and/or particular anatomical targets. The wire 102 may have a size such that the outer diameter (e.g., after application of other outer members) is about 0.008 inches to about 0.040 inches, though larger or smaller sizes may also be utilized depending on particular application needs. For example, particular embodiments may have outer diameter sizes corresponding to standard guidewire sizes such as 0.010 inches, 0.014 inches, 0.016 inches, 0.018 inches, 0.024 inches, 0.035 inches, 0.038 inches, or other such sizes common to guidewire devices. The wire 102 may be formed from stainless steel or other metal or alloy having appropriate mechanical properties. Additionally or alternatively, the wire 102 may be formed from an electrically conductive material of appropriate mechanical properties.

The coupling device 104 may also include or be associated with a transmitter to enable wireless communication between the guidewire system 100 and an external device 110 (or multiple such external devices). In alternative embodiments, the guidewire system 100 and external device 110 may be connected via a wired connection.

The external device 110 may be a hand-held device, such as a mobile phone, tablet, or lap-top computer. Although exemplary embodiments are described herein as using hand-held or mobile devices as the external devices 110, it will be understood that this is not necessary, and other embodiments may include other "non-mobile" devices such as a desktop computer, monitor, projector, or the like. In some embodiments, the external device 110 includes a mobile/hand-held device and additionally includes a desktop device or other non-mobile device. For example, a mobile device may be configured to receive transmitted data from the transmitter and function as a bridge by further sending the data to the non-mobile computer system. This may be useful in a situation where the physician would like the option of viewing data on a mobile device but may need to have the data additionally or alternatively passed or mirrored on a larger monitor such as when both hands are preoccupied (e.g., while handling the guidewire system 100).

The external device 110 of the guidewire system 100 may assist the physician in determining a position of the distal tip of the wire 102 within a vessel or other targeted anatomy of the human body. In this manner, the physician can appropriately position the wire 102 while also obtaining data of various parameters at the targeted anatomy so that the physician can better understand the relevant environment and make appropriate decisions while treating a patient.

The wireless system(s) may include, for example, a personal area network (PAN) (e.g., ultra-high frequency radio wave communication such as Bluetooth®, ZigBee®, BLE, NFC), a local area network (LAN) (e.g., WIFI), or a wide area network (WAN) (e.g., cellular network such as 3G, LTE, 5G). Wireless data transmission may additionally or alternatively include the use of light signals (infrared, visible radio, with or without the use of fiber optic lines), such as radiofrequency (RF) sensors, infrared signaling, or other means of wireless data transmission.

As used herein, "electrical signals" and "signals" both refer generally to any signal within a disclosed system, device, or method. Whereas, "sensor data signal," "sensor signal," or "data signal" refers to any signal that carries commands or information generated by a medical device, such as a medical sensor. In contrast, "power signal" or "energy signal" refers to any signal that provides power to a medical device, such as a sensor. In some cases, a "signal" may comprise both a data signal and a power signal.

Processing of sensor data signals may be fully or primarily carried out at the external device 110, or alternatively may be at least partially carried out at one or more other external devices communicatively connected to the external device 110, such as at a remote server or distributed network. Additionally or alternatively, sensor data signals may be processed at the coupling device 104, on the wire 102, or at some combination of devices within the guidewire system 100. Sensor data signals may include, for example, image data, location data, and/or various types of sensor data (as related to fluid flow, fluid pressure, presence/levels of various gases or biological components, temperature, other physical parameters, and the like).

As explained in greater detail below, one or more sensors may be coupled to the wire 102, and the one or more sensors can operate to send data signals through the wire 102 to the coupling device 104. Additionally, or alternatively, the coupling device 104 may operate to send power or signals to the one or more sensors.

Figure 2:
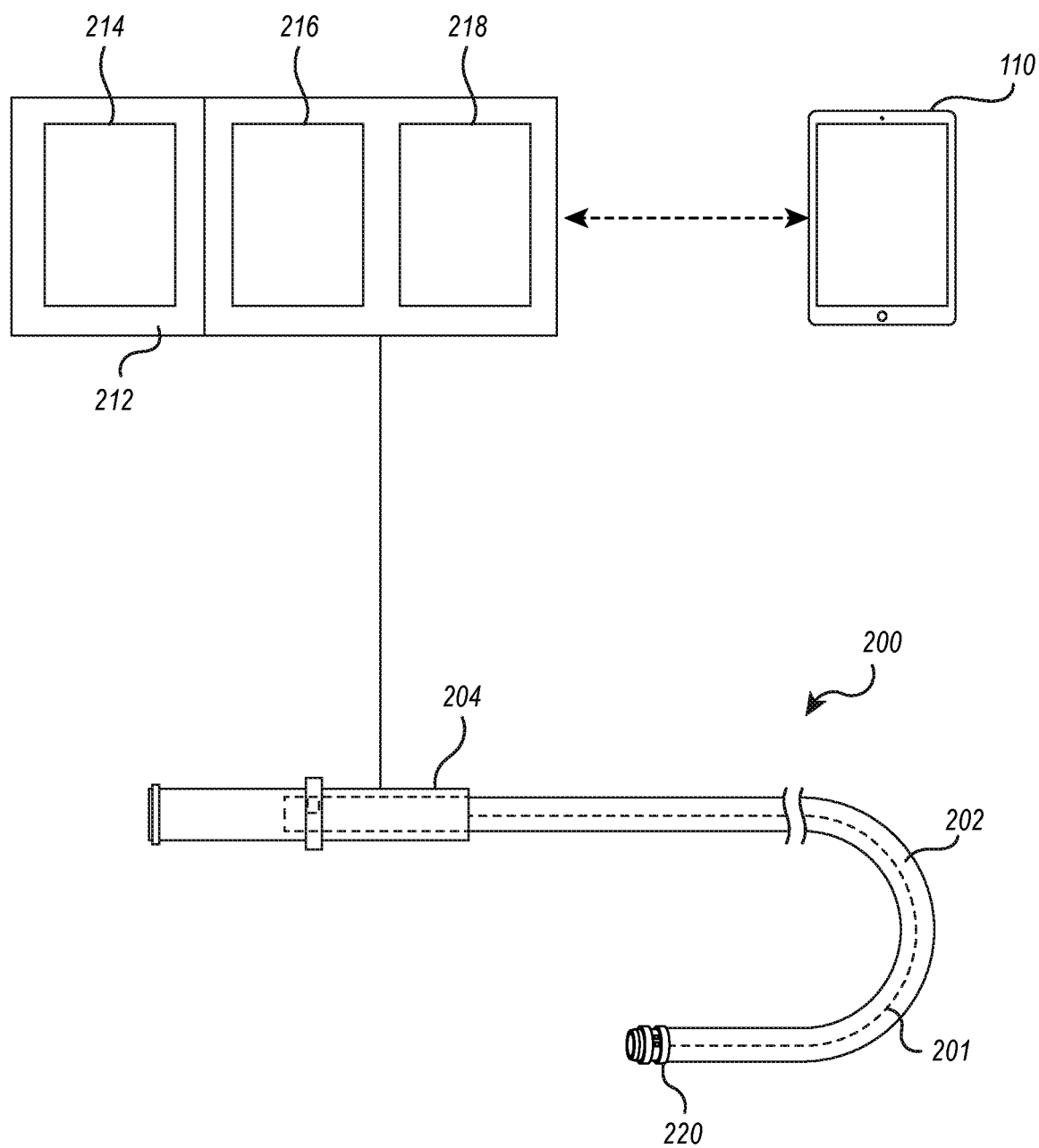
FIG. 2 illustrates a catheter system configured to provide one or more of the features described herein, showing components of a power and data coupling device and showing that the coupling device may be communicatively coupled to an external device.

FIG. 2 is an overview of a catheter system 200 that may incorporate one or more of the features described herein. The catheter system 200 may be similar to the guidewire system 100 in many respects, and the above description related to the guidewire system 100 is also applicable here except where differences are specified.

The catheter system 200 includes a catheter 202 and a proximal device 204 (which may also be referred to herein as "the power and data coupling device 204" or just "the coupling device 204"). The coupling device 204 includes a control unit 212 (shown enlarged and in schematic form) that includes a power source 214, data signal processor 216, and optionally a transmitter 218. The transmitter 218 enables wireless communication to the external device 110 (or multiple such devices) as described above with respect to FIG. 1. As used herein, the catheter 202 may also be referred to as a type of elongated conductive member.

The data signal processor 216 is configured to receive sensor data signals, sent through the catheter 202, from one or more sensors 121, 220 associated with the catheter 202. The power source 214 is configured to transmit power through the catheter 202 to power the one or more sensors 121, 220 and/or other components of the catheter 202. The power source 214 may include an on-board power source, such as a battery or battery pack, and/or may include a wired connection to an outside power source. The one or more sensors 220 may be located at any suitable position on the catheter 202 but will typically be disposed at the distal section of the catheter 202 expected to reach the targeted anatomy. Sensors 220 may be coupled to the catheter 202 by employing bonding, molding, co-extrusion, welding and/or gluing techniques, for example.

Power lines and/or data lines 201 extend along the length of the catheter 202 to the one or more sensors 220. As used herein, a "power line" and/or "data line" refer to any electrically conductive pathway (e.g., traces) within the medical device. Although multiple power and/or data lines 201 may be utilized, preferred embodiments are configured to send both power and data on a single line and/or manage sensor data signals from multiple sensors on a single line. This reduces the number of lines that must be routed through the structure of the catheter 202 and more effectively utilizes the limited space of the device, as well as reducing the complexity of the device and the associated risk of device failure. Additionally, as used herein, an "un-wired sensor" (in either the guidewire system 100 or in the catheter system 200) refers to a sensor that does not have a physically continuous connection, via one or more power lines and/or data lines, that connect the sensor to a power source and/or an external device 110.

The proximal device 204 may include one or more ports to facilitate the introduction of fluids (e.g., medications, nutrients) into the catheter 202. The catheter 202 may be sized and configured to be temporarily inserted in the body, permanently implanted in the body, or configured to deliver an implant in the body. In one embodiment, the catheter 202 is a peripherally inserted central catheter (PICC) line, typically placed in the arm or leg of the body to access the vascular system of the body. The catheter 202 may also be a central venous catheter, an IV catheter, coronary catheter, stent delivery catheter, balloon catheter, atherectomy type catheter, or IVUS catheter or other imaging catheter. The catheter 202 may be a single-lumen or multi-lumen catheter.

Figure 3A:
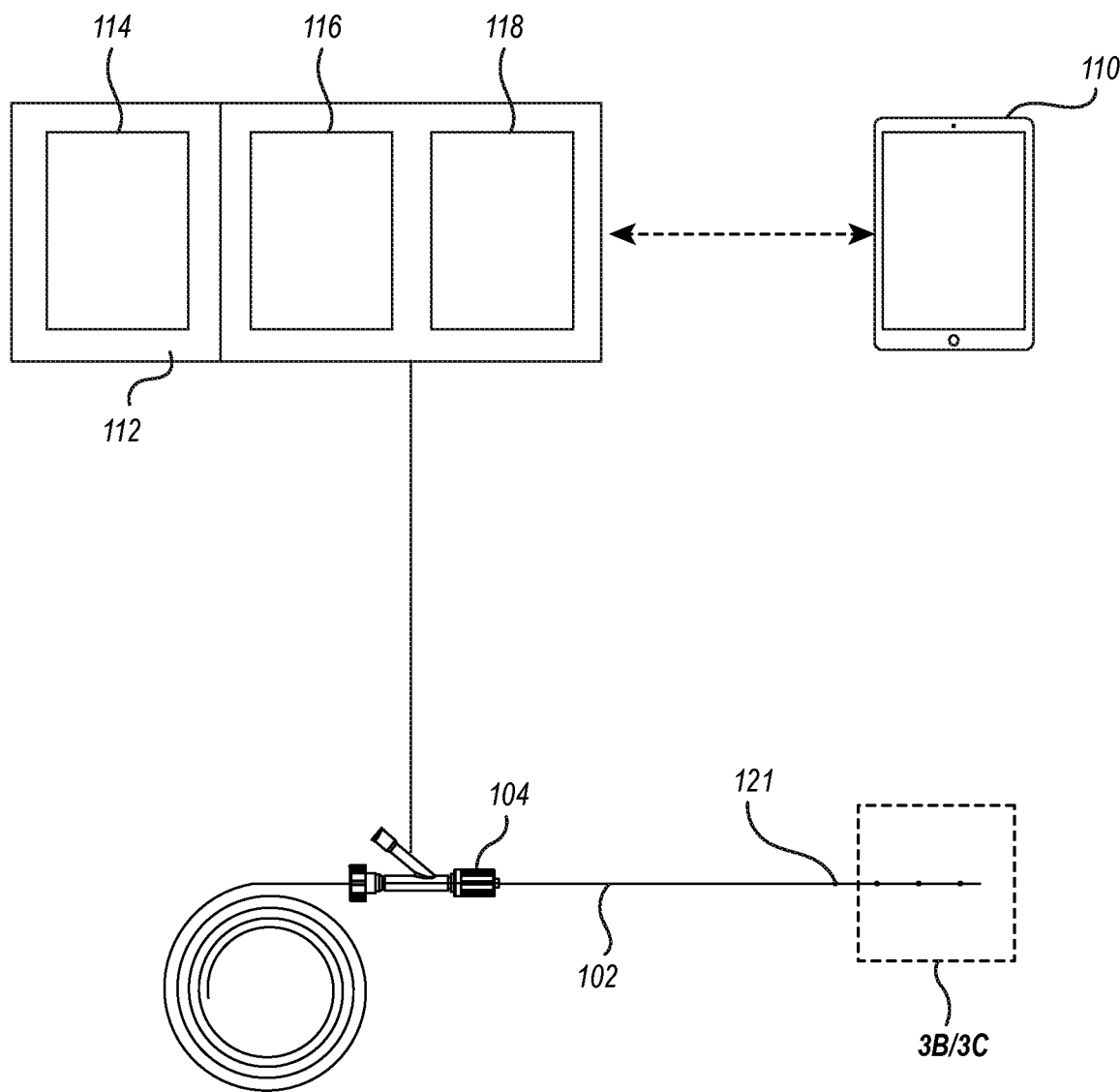
FIG. 3A illustrates a more detailed view of the guidewire system of FIG. 1, showing components of a power and data coupling device and showing that the coupling device may be communicatively coupled to an external device.

FIG. 3A provides another view of the guidewire system 100 of FIG. 1. The guidewire system 100 shares certain features with the catheter system 200, and the description of common parts is therefore applicable to the guidewire system 100 as well. As shown, the guidewire system 100 includes a control unit 112 (shown enlarged and in schematic form) that includes a power source 114, data signal processor 116, and optionally a transmitter 118. The transmitter 118 enables wireless communication to the external device 110 (or multiple such devices) as described above.

The data signal processor 116 is configured to receive sensor data signals, sent through the wire 102, from one or more sensors 121 associated with the guidewire 102. The power source 114 is configured to transmit power through the wire 102 to power the one or more sensors 121 and/or other components of the wire 102. The power source 114 may include an on-board power source, such as a battery or battery pack, and/or may include a wired connection to an outside power source. The one or more sensors 121 may be located at any suitable position on the wire 102 but will typically be disposed at the distal section expected to reach the targeted anatomy. As used herein, the "distal section" or "distal portion" refers to the distal-most 30 cm of the device, the distal-most 20 cm of the device, the distal-most 15 cm of the device, the distal-most 10 cm of the device, or to a range using any two of the foregoing values as endpoints. In some embodiments, the "intermediate section" may be considered as roughly the middle third of the device, and the "proximal section" or "proximal portion" may be considered as roughly the proximal third of the device.

Unlike the catheter system 200, the guidewire system 100 is configured to send these power and data signals through the actual wire 102 itself. In some embodiments, multiple power and/or data signals (e.g., data signals from multiple sensors 121) can be sent through the wire 102 simultaneously. Power and/or data signals can also be sent in a "continuous" fashion. That is, the power and/or data signals can have a sufficiently high sampling rate such that the information is provided to the user within time frames that are practically "real-time". For most applications, this will include sampling rates of approximately 5 seconds or less, 3 seconds or less, 1 second or less, or sub-second sampling rates.

Using the wire 102 itself to send power and/or data signals through the device provides several benefits. For example, using the wire 102 to transmit these signals reduces or eliminates the need to run other connection lines along the wire 102 to connect the sensors 121 to the proximal portion and/or to deliver power to the sensors. Given the fact that guidewires inherently involve strict dimensional and performance (e.g., torqueability, bending, pushability, stiffness, etc.) limitations and have limited space to work in, the ability to reduce or eliminate extraneous components frees up limited space and allows greater design flexibility. Reducing or eliminating the use of additional connection lines also reduces the overall complexity of the device and thereby reduces the risk of component failure, leading to a more robustly functional device.

Additional Sensor Details

The one or more sensors 121 of the guidewire system 100 and/or the one or more sensors 220 of the catheter system 200 may include a pressure sensor, flow sensor, imaging sensor, or a component detection sensor, for example. A pressure sensor (or multiple pressure sensors) may be sized and configured to sense changes in pressure in the environment. A flow sensor (or multiple flow sensors) may be sized and configured to sense the fluid flow, such as velocity or other flow characteristics. A detection sensor (or multiple detection sensors) may detect a proximity or distance to one or more detection nodes positioned external relative to the body. An imaging sensor may gather various forms of imaging data.

The one or more sensors may additionally or alternatively be configured to sense the presence of biological components or measure physiological parameters in the targeted anatomical location (e.g., in the blood). Example biological components that may be detected/measured include sugar levels, pH levels, $CO_2$ levels ($CO_2$ partial pressure, bicarbonate levels), oxygen levels (oxygen partial pressure, oxygen saturation), temperature, and other such substrates and physiological parameters. The one or more sensors may be configured to sense the presence, absence, or levels of biological components such as, for example, immune system-related molecules (e.g., macrophages, lymphocytes, T cells, natural killer cells, monocytes, other white blood cells, etc.), inflammatory markers (e.g., C-reactive protein, procalcitonin, amyloid A, cytokines, alpha-1-acid glycoprotein, ceruloplasmin, hepcidin, haptoglobin, etc.), platelets, hemoglobin, ammonia, creatinine, bilirubin, homocysteine, albumin, lactate, pyruvate, ketone bodies, ion and/or nutrient levels (e.g., glucose, urea, chloride, sodium, potassium, calcium, iron/ferritin, copper, zinc, magnesium, vitamins, etc.), hormones (e.g., estradiol, follicle-stimulating hormone, aldosterone, progesterone, luteinizing hormone, testosterone, thyroxine, thyrotropin, parathyroid hormone, insulin, glucagon, cortisol, prolactin, etc.), enzymes (e.g., amylase, lactate dehydrogenase, lipase, creatine kinase), lipids (e.g., triglycerides, HDL cholesterol, LDL cholesterol), tumor markers (e.g., alpha fetoprotein, beta human chorionic gonadotrophin, carcinoembryonic antigen, prostate specific antigen, calcitonin), and/or toxins (e.g., lead, ethanol).

Unless stated otherwise, when reference is made to sensors (either generically or to a specific type of sensor) it should be understood to be inclusive of the supporting electronics as well. Supporting electronics may include, for example, power regulators, converters, signal amplifiers, processing components such as application-specified integrated circuits (ASICs), field-programmable gate arrays (FPGAs), and the like. The supporting electronics of the one or more sensors 121 are preferably positioned near the one or more sensors 121 themselves (e.g., at the distal section of the wire 102 on a substrate). This was beneficially found to reduce signal drift as compared to placing the supporting electronics at the proximal sections of the device. Placing the supporting electronics (e.g., ASICs) on the distal portion of the wire 102 near the sensors 121, and using the wire 102 itself as the means of transmitting data signals to the proximal end, provides effective signal transmission without the significant drift problems of other approaches.

Guidewire Sensor Arrangement & Distal Features

FIG. 3B illustrates an expanded view of the distal section of the guidewire system 100 of FIG. 3A, showing various sensors arranged thereon. In this embodiment, the one or more sensors 121, 220 include multiple pressure sensors 120 and ultrasound sensors 122. These sensors are positioned on a substrate 124 and the substrate 124 is positioned on the wire 102 in a manner that places the sensors at their respective desired positions. The substrate 124 may be made of a somewhat flexible material (e.g., a suitable medical grade polymer) that allows wrapping, winding, or otherwise positioning the substrate 124 onto the wire 102. The substrate 124 also includes flexible circuitry such as trace lines and/or one or more conductive contacts to couple the sensors to the underlying wire 102. The substrate 124 can form a friction fit with the wire 102 and can additionally or alternatively be mechanically bonded to the wire 102.

Coupling the sensors to the substrate 124 and then placing the substrate 124 on the wire 102 provides several benefits. For example, the substrate 124 can be spread into what is essentially a 2-dimensional layout, which makes it much easier to appropriately position the sensors. The 2-dimensional substrate 124, with sensors coupled thereto, can then be placed on the 3-dimensional cylindrical shape of the wire 102 more readily than placing each sensor separately onto the wire 102. In particular, it is easier to ensure that the various sensors are appropriately positioned relative to one another on the substrate 124 and then to position the substrate 124 onto the wire 102 than to attempt to control relative spacing of each sensor on the 3-dimensional cylindrical shape of the wire 102. One will appreciate, however, that in at least one embodiment, the various sensors can be directly placed on the 3-dimensional wire 102 without the benefit of a 2-dimensional substrate 124. Alternatively, the various sensors can be placed on the substrate after the substrate has been applied to the 3-dimensional wire 102.

The illustrated embodiment also includes an outer member 126 (shown here with dashed lines) that can be positioned over the sensor-containing portion of the wire 102. The outer member 126 may be formed from a suitable medical grade polymer (e.g., polyethylene terephthalate (PET) or polyether block amide (PEBA). The outer member 126 can function to further constrain and maintain position of the sensors and/or to smooth over the outer surface for a more uniform outer diameter. The outer member 126 may be applied by shrink-fitting a tube in place, by dip coating, and/or through other manufacturing methods known in the art. A hydrophilic coating may also be added to the outer surface of the device.

Figure 3C:
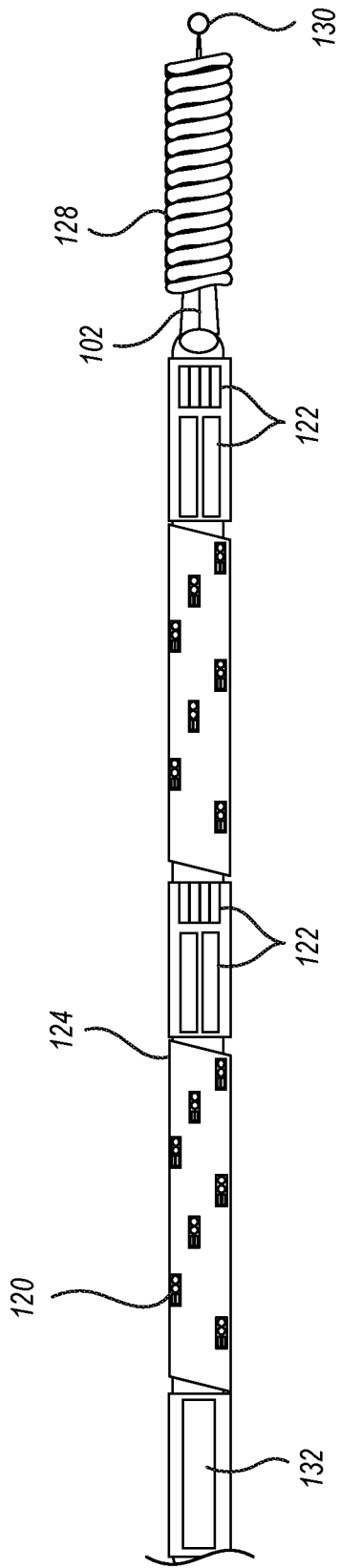
FIG. 3C is a schematic view of a distal section of the guidewire to illustrate additional distal components and features of the device.

FIG. 3C illustrates another, schematic view of the distal section of the guidewire system 100 shown in FIG. 3A, showing multiple pressure sensors 120 and multiple ultrasound sensors 122 disposed on the substrate 124, which is positioned on the wire 102. As shown, the distal-most section of the device can also include a coil 128 and/or atraumatic tip 130. The coil 128 may be a single coil or multiple connected or interwoven coils. Additionally or alternatively, a polymer material may be positioned on or applied to the distal section of the wire 102. Additionally, or alternatively, a polymer material may be positioned on or applied to the distal section of the wire 102. The atraumatic tip 130 forms a sphere or other curved shape to protect against trauma potentially caused by the distal portion of the wire 102. The atraumatic tip 130 may be formed from a polymer adhesive material and/or solder, for example.

As shown, the wire 102 can include a grind profile such that more distal sections of the wire 102 progress to smaller diameters. For typical guidewire sizes (e.g., 0.014 inches, 0.018 inches, 0.024 inches), the wire 102 may progress to a diameter of about 0.002 inches at the distal end. The distal end of the wire 102 may also be flattened to form a standard "ribbon" shape.

The illustrated embodiment also includes an energy harvester 132. The energy harvester is configured to convert power signals traveling within the wire 102 into regulated DC voltages suitable for the sensors. The energy harvester 132 can also provide other electrical regulation functions such as cutting power to the sensors during a fault or brownout, for example. Additionally, as used herein and unless specified otherwise, the energy harvester 132 is considered a subcomponent of the one or more sensors 121. As such, unless stated otherwise, references to the one or more sensors 121 also refer to the associated circuitry, such as the energy harvester 132.

Additionally, in at least one embodiment, the energy harvester is configured to provide control functions for the one or more sensors 121. For example, a particular signal can be communicated from the power and data coupling device 104 to the energy harvester. The particular signal may comprise a chirp, an impulse function, or some signal at a particular frequency channel. The energy harvester maps the particular signal to a predetermined command and then acts upon that predetermined command. For example, a particular signal may map to a command to cut DC power to one or more rails that are powering one or more sensors. As such, upon receiving the particular signal, the energy harvester stops providing power to the one or more sensors causing the one or more sensors to turn off. Any number of different signals may be mapped to any number of different commands. Additionally, in at least one embodiment, a circuit other than the energy harvester receives, interprets, and/or acts upon the signals.

The length of the wire 102 that includes the substrate 124 (and thus includes sensors) may be about 3 cm to about 30 cm, or more typically about 5 cm to about 15 cm, though these lengths may be varied according to particular application needs. As explained below with respect to the example of FIGS. 4A through 4D, in preferred embodiments the length of the sensor arrangement substantially spans the expected length of lesions/stenoses or other target anatomy. The linear arrangement of pressure sensors 120 can be utilized to provide pressure mapping at targeted anatomy without the need to move the wire 102. Multiple measurements from multiple sensors may be conducted simultaneously and/or continuously. The arrangement of pressure sensors 120 can also be utilized to measure pulse wave velocity (PWV) (e.g., by determining a series of wave peaks and measuring time between peaks) and/or to provide spatial tracking of a pulse waveform.

Methods of Localization within Target Anatomy

FIGS. 4A through 4D illustrate a sequence showing use of the guidewire system 100 to effectively guide positioning and deployment of a medical device at a targeted anatomical location. In this particular example, the guidewire system 100 is used to properly position a stent 406 at a targeted stenosis 404.

Figure 4A:
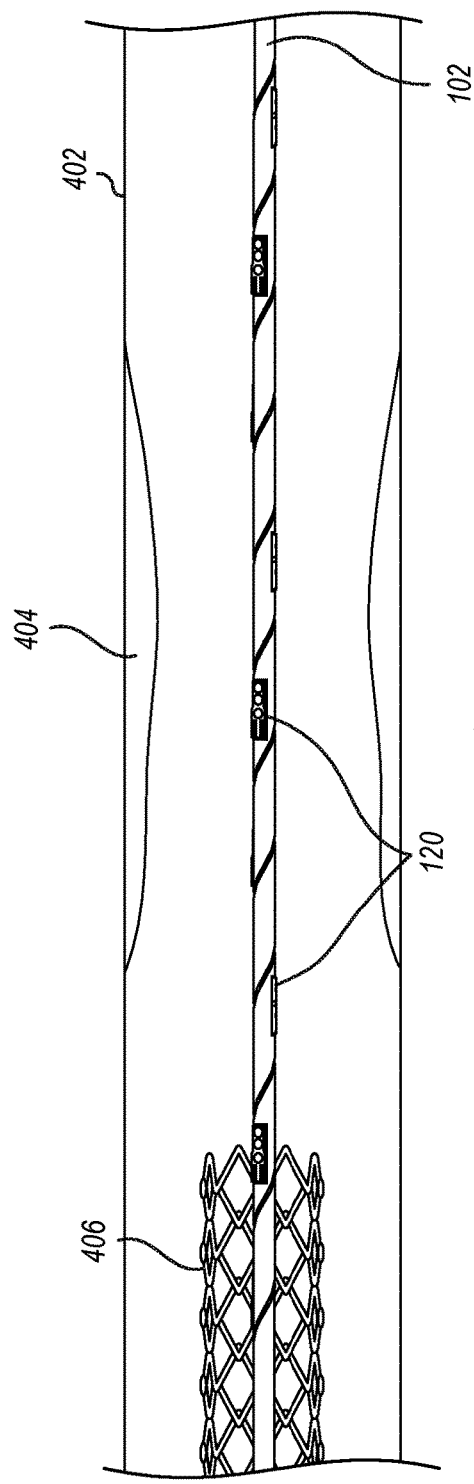

FIG. 4A shows the wire 102 with pressure sensors 120 (other components removed for better visibility) positioned within a vessel 402. The wire 102 is routed through the vessel 402 to a position where the arrangement of pressure sensors 120 span or at least substantially coincide with the stenosis 404. The linear arrangement of the pressure sensors 120 allows the wire 102 to be effectively positioned coincident with the stenosis 404 because the stenosis 404 will cause pressure differences at that portion of the vessel 402, and the user can advance the wire 102 until those pressure differences are read by the sensors 120. For example, where the vessel 402 is a coronary artery, the pressure distal of the stenosis 404 will be somewhat lower than the pressure proximal of the stenosis 404. The wire 102 can be advanced until one or more of the distal-most pressure sensors reach the region of different pressure (e.g., somewhat lower pressure in a coronary vessel stenosis).

The stent 406 is then delivered over the wire 102 toward the stenosis 404. The position of the stent 406 relative to the wire 102 can be determined based on readings from the pressure sensors 120. For example, as the stent 406 is moved distally it will sequentially begin to pass over the pressure sensors 120, causing a change in the pressure reading of the sensors and thereby allowing the user to determine the position of the stent 406 relative to the wire 102.

Figure 4B:
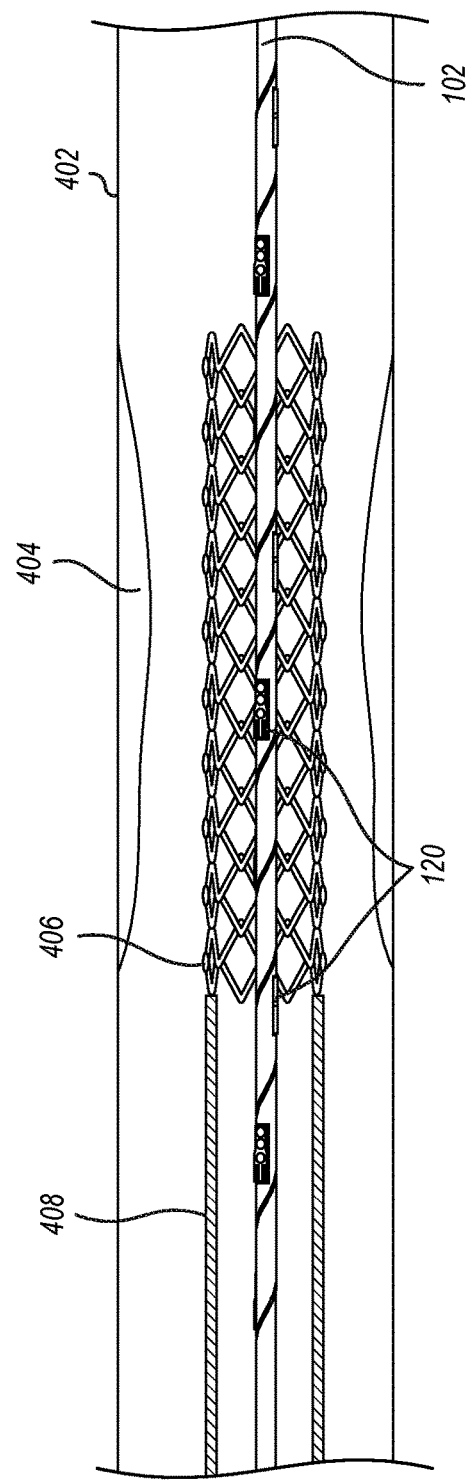

FIG. 4B shows the stent 406 positioned farther within the vessel 402 to its target location. The delivery catheter 408 is also shown. For stent delivery applications such as shown here, the delivery catheter 408 may be a balloon catheter, or the stent 406 may be a self-expanding stent. Other stent types and stent delivery means as known in the art may be utilized. Proper positioning of the stent 406 is possible because the position of the wire 102 relative to the stenosis 404 is known based upon readings received from the pressure sensors 120. Additionally, determining where the stent 406 is positioned relative to the wire 102 thus allows determination of the position of the stent 406 relative to the stenosis 404.

Once the stent 406 is determined to be in the proper position relative to the target stenosis 404, the stent 406 may be deployed as shown in FIG. 4C. After deployment, the wire 102 may remain in place for a time during post-stent assessment. The wire 102 may then be retracted from the vessel 402, leaving the stent 406 in place as shown in FIG. 4D.

Due to the sensors positioned along the length of the wire 102, the guidewire system 100 can therefore provide a localized reference frame (i.e., a reference frame within the localized anatomy of the target) for guiding positioning of a medical device. This is beneficial because the target anatomy is not always static. In vasculature applications, for example, heartbeats cause the vessel to constantly move. The localized reference frame defined by the distal section of the guidewire system 100 moves substantially with the target anatomy in which it is placed, removing many positioning complications and thereby improving the ability to position stents and/or other medical devices.

This localized reference frame is also relatively stable because the wire 102 does not need to be moved to make sequential measurements. Additionally, the sensors 120 are able to continuously and simultaneously provide sensor data signals during the placement of the stent, or other medical device. This allows a medical practitioner to guide the stent, or other medical device, in real time to the desired position within the body. That is, the linear arrangement of the sensors 120 allows multiple measurements without the need to "pull back" the wire 102 to make measurements in other positions. Moreover, as described above, the system may be configured to provide multiple measurements from multiple sensors simultaneously, eliminating the need to even do a "virtual pull back" of sequential measurements along the length of sensors.

The procedure illustrated in FIGS. 4A through 4D is one example of using the guidewire system 100 for localization within target anatomy. The guidewire system 100 and/or catheter system 200 may be utilized in other applications where the localization features of the system would be beneficial. For example, localization features described herein may be utilized to aid in proper placement of a PICC catheter or central venous catheter at a targeted site such as the cavoatrial junction.

The Conductive Elongated Member as a Power and Data Conductive Path

Figure 5:
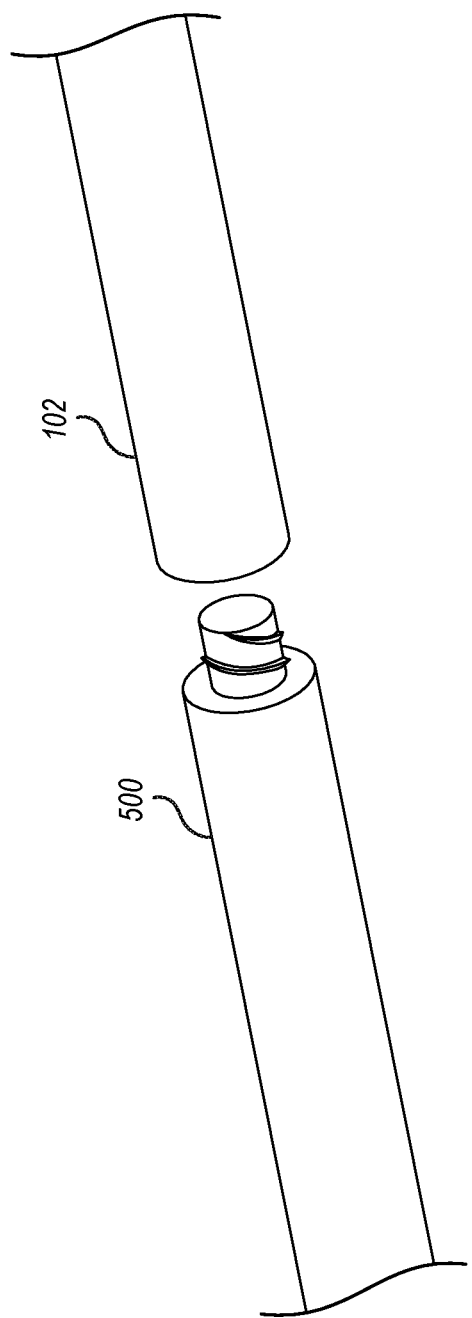
FIG. 5 illustrates an extension wire being added to the wire.

FIG. 5 illustrates an extension wire 500 being added to the wire 102. In various use cases, it may be necessary to extend the wire 102 in order to better position and/or manipulate the wire 102 within a patient's body. The depicted extension wire 500 may be coupled to the wire 102 through any number of different physical couplings, including, but not limited to, a threaded connection, a magnetic connection, a press-fit connection, a snap connection, or an adhesive connection.

In at least one embodiment, the resulting physical coupling results in a continuous conductive pathway from the extension wire 500 to the wire 102. As such, due to at least the physical coupling and the electrical coupling, both the extension wire 500 and the wire 102 may be jointly considered and referred to as the "wire 102." More specifically, electrical signals applied to the extension wire 500 will propagate from the extension wire 500 to the wire 102. Accordingly, unless stated otherwise, all descriptions of the wire 102 provided herein also apply when an extension wire 500 is attached to the wire 102. Additionally, it will be appreciated that any elongated conductive member disclosed herein may comprises multiple extensions that are removably attached to each other.

In at least one embodiment, the guidewire system 100 comprises a medical device system for concurrent power and data transfer. In particular, the guidewire system 100 may comprise a type of elongated conductive member. As used herein, the elongated conductive member comprises a proximal portion and a distal portion. At least a portion of the elongated conductive member is configured for insertion within an intraluminal space. Additionally, both the proximal portion and the distal portion of elongated conductive member may be electrically conductive.

In at least one embodiment, the elongated conductive member comprises a single conductive pathway extending from the proximal portion to the distal portion. For instance, the single conductive pathway may comprise a stainless-steel wire 102 within the guidewire system 100. Additionally, or alternatively, the elongated conductive member comprises multiple conductive pathways extending from the proximal portion to the distal portion. For instance, the catheter system 200 may comprise multiple wires integrated within the structure of the catheter 202. Additionally, in at least one embodiment, the elongated conductive member comprises a first conductive pathway for use as a power channel and a second conductive pathway for user as a signal channel, both the first conductive pathway and the second conductive pathway extending from the proximal portion to the distal portion.

As described above, one or more sensors 121 may be in electrical connection with the elongated conductive member. Additionally, the medical device, which includes the elongated conductive member, may also comprise one or more electrical components that are physically configured such that when activated, the one or more electrical components cause the medical device system to perform various actions. As used herein, the one or more electrical components may comprise discrete circuit components, digital circuit components, analog circuit components, processor(s), or any combination thereof. The one or more electrical components may be integrated within control unit 112 or 212, within the external device 110, and/or on the elongated member. Activating the one or more electrical components may comprise providing power to the one or more electrical components.

In at least one embodiment, the one or more electrical components cause the medical device system to allocate a signal space into a plurality of unique contiguous segments. Each segment within the signal space comprises a portion of the signal space that may be used for the purposes of communicating data, power, or other information. The signal space may comprise a frequency-domain space, a time-domain space, or any other space capable of carrying a signal. Additionally, allocating the signal space may comprise dynamically identifying signal channels of interest. Alternatively, allocating the signal space may comprise providing electrical components that are configured to statically define the signal space.

Figure 6A:
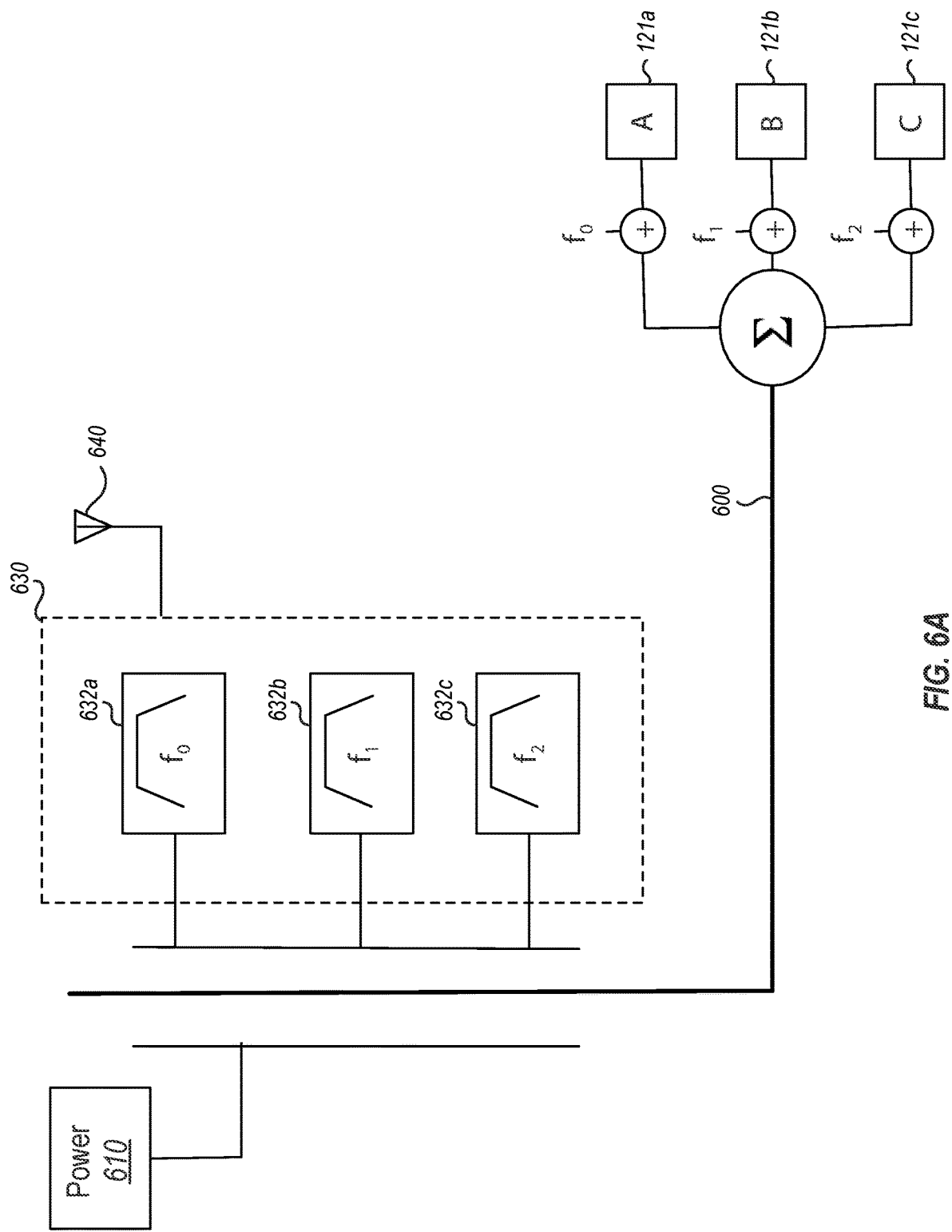
FIG. 6A illustrates an electrical schematic diagram of a medical device.
Figure 6B:
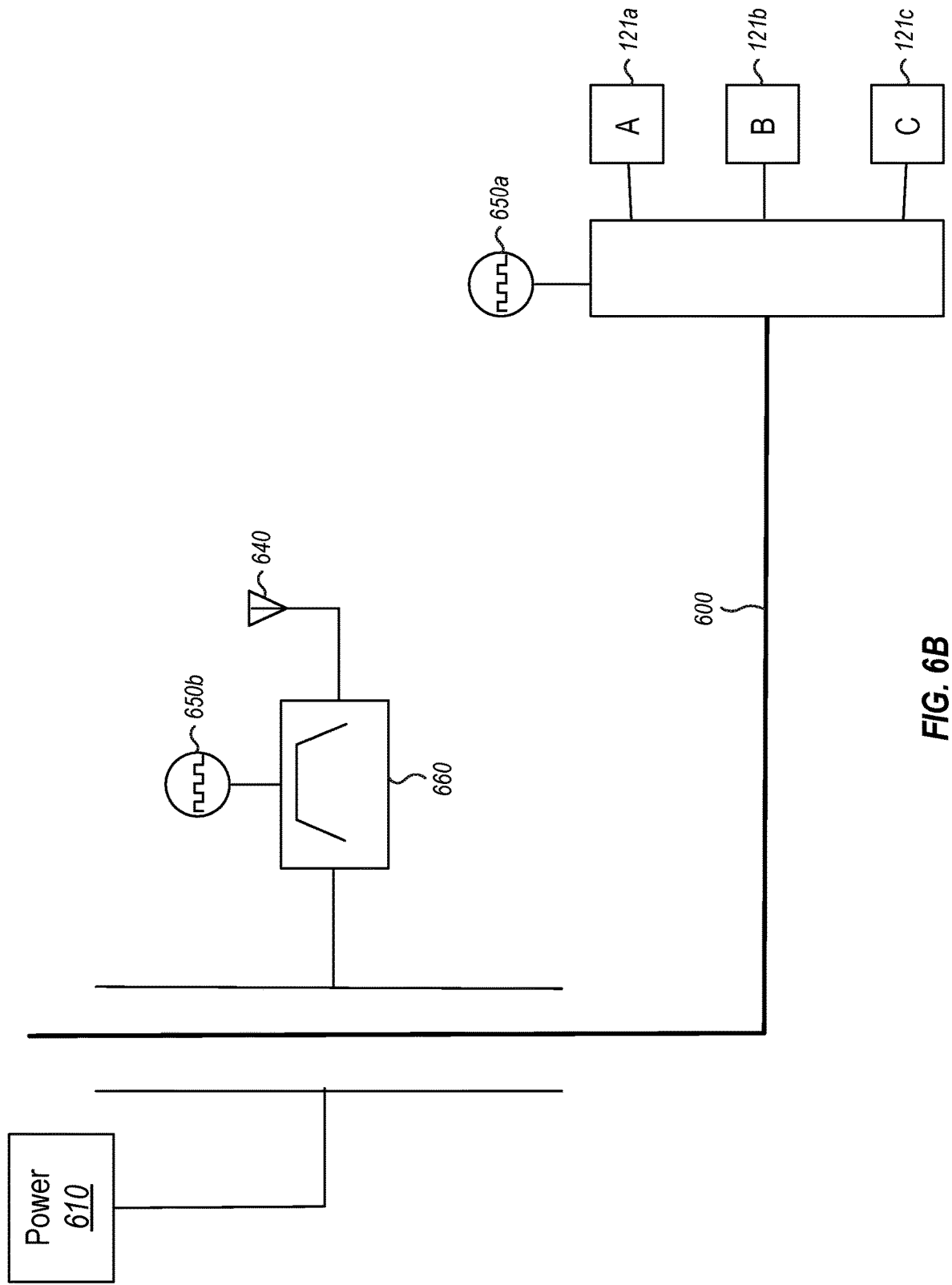
FIG. 6B illustrates another electrical schematic diagram of the medical device.
Figure 7:
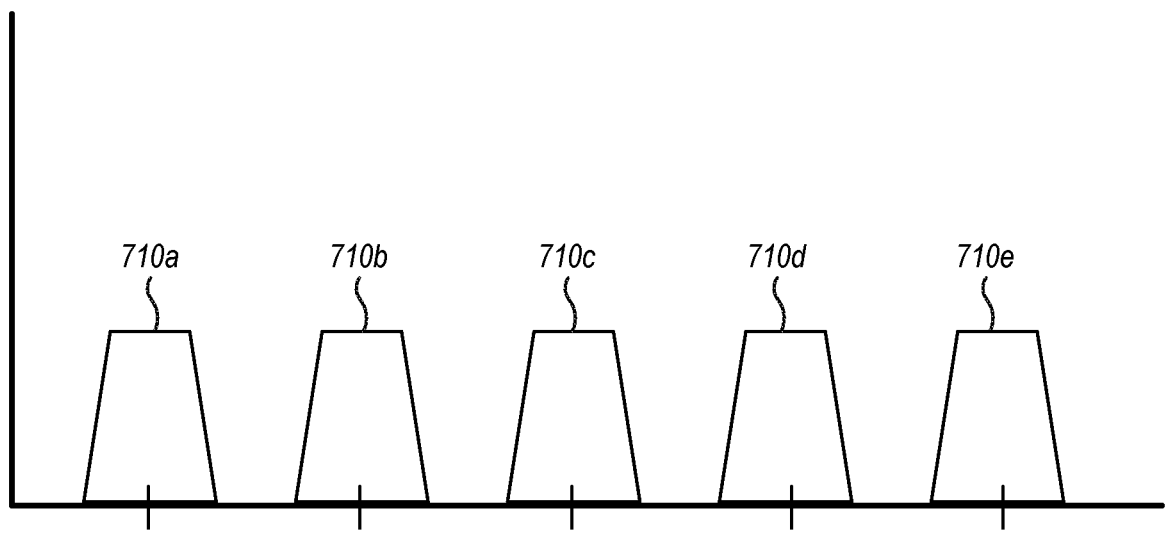
FIG. 7 illustrates channels configured for utilization by the medical device.

For example, FIGS. 6A and 6B illustrate different embodiments of an electrical schematic diagram of the medical device. FIG. 7 illustrates channels configured for utilization by the medical device. In at least one embodiment, the one or more electrical components uniquely allocate each of the plurality of unique contiguous segments to one of (i) one or more power channels or (ii) one or more signal channels. In at least one embodiment, uniquely allocating refers to each contiguous segment being allocated as either a power channel or a signal channel. In some embodiments, there may be multiple power channels and multiple signal channels.

FIG. 6A depicts a schematic of a frequency-based medical device system. In particular, the one or more electrical components cause the medical device system to allocate a signal space into the plurality of unique contiguous segments by designating a plurality of unique contiguous regions of frequency (e.g., 710(a-e)). The one or more electrical components further cause the medical device system to uniquely allocate each of the plurality of unique contiguous regions of frequency to one of (i) the one or more power channels or (ii) the one or more signal channels.

FIG. 6B depicts a schematic of a time-based medical device system. In particular, the one or more electrical components cause the medical device system to allocate a signal space into the plurality of unique contiguous segments by designating a plurality of unique contiguous time slots (e.g., 710(a-e)). The one or more electrical components further cause the medical device system to uniquely allocate each of the plurality of unique contiguous time slots to one of (i) the one or more power channels or (ii) the one or more signal channels.

FIG. 7 illustrates that the signal space 700 may comprise multiple unique contiguous segments in the form of multiple frequency channels 710(a-e). Each frequency channel may be allocated as a power channel for providing power to the electronic devices located on the elongated conductive member or may be allocated as a signal channel for receiving data from the electronic devices on the elongated conductive member. In at least one embodiment, the electronic devices comprise sensors 121, 220.

Additionally or alternatively, the signal space 700 may comprise multiple unique contiguous segments in the form of time slots 710(a-e). Each time slot may be defined based on a clock. Additionally, each time slot may be allocated as a power channel for providing power to electronic devices located on the elongated conductive member or may be allocated as a signal channel for receiving data from the electronic devices on the elongated conductive member.

For example, FIGS. 6A and 6B depict an elongated conductive member 600 that is coupled to a power source 610. The power source 610 may be configured to send electrical signals, via the elongated conductive member 600, to one or more sensors 121(a-c) that are in electrical connection with the elongated conductive member 600. In particular, the power source 610 may send AC electrical signals within a particular unique contiguous segment, such as frequency channel 710a. In at least one embodiment, the elongated conductive member 600 is capacitively coupled to the power source 610 such that no direct physical contact is present between the elongated conductive member 600 and the power source 610. Alternatively, in at least one embodiment, a direct physical contact may be present between the elongated conductive member 600 and the power source 610.

Returning now to FIG. 3C, an elongated conductive member, in the form of the wire 102, is shown to include an energy harvester 132. As used herein, an energy harvester 132 refers to an electronic circuit that is configured to harvest energy from an allocated power channel. In particular, an energy harvester 132 may comprise an electronic circuit to harvest energy from the electrical signals within at least one of the one or more power channels—in this example, frequency channel 710a. The harvested energy is then provided to the at least one of the one or more sensors 121.

In at least one embodiment, the power source 610 transmits energy within the at least one of the one or more power channels and provides power to all of the one or more sensors 121 through the at least one of the one or more power channels. As such, each sensor of the one or more sensors harvests energy from the particular unique contiguous segment of the signal space that is represented by the at least one of the one or more power channels.

Additionally or alternatively, in at least one embodiment, the power source 610 transmits energy within a first power channel of the one or more power channels (e.g., 710a), wherein the first power channel of the one or more power channels comprises a first unique contiguous segment of the signal space. Additionally, the power source 610 transmits energy within a second power channel of the one or more power channels (e.g., 710b), wherein the second power channel of the one or more power channels comprises a second unique contiguous segment of the signal space. The elongated conductive member 600 then provides energy to a first subset of the one or more sensors through the first power channel of the one or more power channel. Each sensor of the first subset of the one or more sensors is configured to harvest energy from the first unique contiguous segment of the signal space. Similarly, the elongated conductive member 600 provides energy to a second subset of the one or more sensors through the second power channel of the one or more power channels. Each sensor of second subset of the one or more sensors is configured to harvest energy from the second unique contiguous segment of the signal space.

Accordingly, in at least one embodiment, the elongated conductive member 600 provides different sets of sensors power through independent power channels. This provides a user with the ability to selectively activate all of the sensors simultaneously or to only activate subsets of the sensors at different times. Additionally, the one or more sensors may comprise at least a first sensor of a first type and a second sensor of a second, different type. Accordingly, in at least one embodiment, a user can activate sensors based upon sensor type. As disclosed herein, this selective control of the sensors and communication with the sensors may be performed over a single conductive path, such as wire 102.

Once at least one sensor from the one or more sensors 121 begins to receive the harvested energy, the at least one sensor will begin to generate data signals based upon readings received by the at least one sensor. FIG. 6A depicts a set of sensors 121(*a-c*) that each transmit along the elongated conductive member 600 at a particular frequency. For example, sensor 121a is summed with any other data signals that are each in their own frequency. One will appreciate that this system allows multiple data signals to be communicated simultaneously in parallel via the elongated conductive member 600.

Additionally, FIG. 6A shows that the one or more electrical components cause the medical device system to isolate transmitted data signals from at least one of the one or more signal channels. As stated above, the data signals are transmitted via the elongated conductive member 600 and generated by the one or more sensors 121(*a-c*). The elongated conductive member 600 is also coupled with a power and data coupling device 630 (also referred to as a proximal device 104 in FIG. 1 and a proximal device 204 in FIG. 2). In at least one embodiment, the elongated conductive member 600 is capacitively coupled to the power and data coupling device 630 such that no physical connection is present between the elongated conductive member 600 and the power and data coupling device 630. Alternatively, in at least one embodiment, a physical connection may be present between the elongated conductive member 600 and the power and data coupling device 630.

The power and data coupling device 630 comprises multiple frequency filters 632(*a-c*) that allow it to isolate the respective data signals that are communicated along the elongated conductive member 600. Additionally, or alternatively, in at least one embodiment, the power and data coupling device 630 isolates multiple transmitted data signals in parallel. Each data signal from the multiple data signals is associated with a different unique contiguous region of frequency selected from the plurality of unique contiguous regions of frequency. The power and data coupling device 630 further comprises a transmitter 640 that is configured to communicate the isolated data signals to the external device 110 for display and/or processing.

FIG. 6B depicts a set of sensors 121(*a-c*) that each transmit along the elongated conductive member 600 within a time slot. For example, each sensor 121(*a-c*) communicates data signals via the elongated conductive member 600 at a particular time slot that is determined by a clock signal 650a. Additionally, FIG. 6B shows that the elongated conductive member 600 is also coupled with a power and data coupling device 630. The power and data coupling device 630 comprises a filter 660 that is in communication with a clock 650b, which clock is synchronized with clock 650a. The combination of the synchronized clocks 650a, 650b and the filter 660 allow the power and data coupling device 630 to isolate the data signals within each respective time slot. The power and data coupling device 630 further comprises a transmitter 640 that is configured to communicate the isolated data signals to the external device 110 for display and/or processing.

In at least one embodiment, the power and data coupling device 630 comprises an indicator for indicating information relating to the operation of the power and data coupling device 630 or the conductive elongated member. The indicator may comprise an audible alert, a haptic alert, a visual alert (e.g., a light), a communication to an external device that performs an alert function and/or any other type of alert. For example, the transmitter 640 may comprise some processing capability that can detect an interruption in power traveling through the power and data coupling device 104 and/or a poor quality of data signals being received by the power and data coupling device 104. In such cases, the power and data coupling device 104 may cause an indication of an alert to be issued in order to notify a user of the issue.

One will appreciate that while FIG. 7 depicts a single dimensional signal space 700, in at least one embodiment, the signal space 700 may comprise a multiple dimensional signal space 700. For example, the signal space 700 may utilize a QPAM, QPSK, Viterbi codes, or other signal space.

FIGS. 8A-8C depicts various signal schematic diagrams of the guidewire system 100. One will appreciate, however, that similar electrical circuits could also be integrated into any elongated conductive member 600, including a catheter 202. The schematic of FIG. 8A depicts a circuit for gathering and displaying arterial pressure. In particular, the arterial pressure 802 is gathered by a capacitive pressure sensor 806, one will appreciate that any number of different pressure sensors types may alternatively be used. The capacitive pressure sensor 806 utilizes a capacitance-to-voltage converter 804 to generate a particular voltage based upon the particular capacitance that is measured by the capacitive pressure sensor 806.

The particular voltage is processed through a voltage-controlled oscillator ("VCO") 808 to generate a particular waveform. The particular waveform is then transmitted via the elongated conductive member 600 from the distal portion of the elongated conductive member 600 to the proximal portion of the elongated conductive member 600. In this example, the elongated conductive member 600 comprises the wire 102 within the guidewire system 100. In at least one embodiment, the particular waveform is transmitted within a particular unique contiguous segment of a signal space, such as a signal channel as defined by a particular frequency channel.

Once the particular waveform reaches the proximal portion of the elongated conductive member 600, a capacitive pickup 810 detects the particular waveform within the particular unique contiguous segment of a signal space. In at least one embodiment, the capacitive pickup 810 is integrated within the power and data coupling device 630. In at least one embodiment, the power and data coupling device 630 may be in capacitive communication with the elongated conductive member 600 through changing electric fields. The capacitive pickup 810 communicates the detected waveform to a phase-lock loop (PLL) 812 which is then turned into a voltage 814. The resulting voltage 814 can then be processed and displayed 816 as a pressure reading to an end-user.

FIG. 8B depicts a circuit for gathering and displaying a pulse echo. In particular, the pulse echo is gathered by an ultrasound pulse echo sensor 818. The ultrasound pulse echo sensor 818 generates an amplitude modulated wave 820. A voltage envelope versus time 822 is then created. In at least one embodiment, the voltage envelope versus time is created using a Hilbert transform circuit. The resulting signal is processed through a voltage-controlled oscillator ("VCO") 824 to generate a representative signal. The representative signal is then transmitted via the elongated conductive member 600 from the distal portion of the elongated conductive member 600 to the proximal portion of the elongated conductive member 600. Similar to the above example, in this example, the elongated conductive member 600 comprises the wire 102 within the guidewire system 100. In at least one embodiment, the representative signal is transmitted within a particular unique contiguous segment of a signal space, such as a signal channel as defined by a particular frequency channel.

Once the particular waveform reaches the proximal portion of the elongated conductive member 600, a capacitive pickup 826 detects the representative signal within the particular unique contiguous segment of a signal space. In at least one embodiment, the capacitive pickup 826 is integrated within the power and data coupling device 630. Additionally, the power and data coupling device 630 may be in capacitive communication with the elongated conductive member 600 through changing electric fields. The capacitive pickup 826 communicates the detected signal to a phase-lock loop (PLL) 828 which is then turned into a voltage 830. The resulting voltage 830 can then be processed and displayed 832 as a pulse echo reading to an end-user.

FIG. 8C depicts a circuit for providing power to the one or more sensors 121. As such, in contrast to FIGS. 8A and 8B, FIG. 8C starts from the proximal portion of the elongated conductive member 600 and transmits towards the distal portion of the elongated conductive member 600. In particular, a frequency generation circuit 834 creates a power signal within a particular unique contiguous segment of a signal space, the particular unique contiguous segment comprising a particular power channel. The generated AC signal is communicated to a power amplifier 836 to generate a particular AC power signal within the particular power channel. The AC power signal is capacitively coupled 838 to the elongated conductive member 600 and then transmitted, via the elongated conductive member 600, to the one or more sensors 121 at the distal portion of the elongated conductive member 600.

Once the AC power signal reaches the distal portion of the elongated conductive member 600, the AC power signal is rectified 840 and processed through a qualification/smoothing circuit 842. The resulting DC power signal 844 is then provided to the one or more sensors 846, 121, 220.

One will appreciate that each of the above-described circuits in FIGS. 8A-8C utilize the capacitive coupling between the elongated conductive member 600 and the power and data coupling device 630. As such, the describes sensors can be provided power and can communicate data to an external device 110 without requiring a physical connection between the power and data coupling device 630 and the elongated conductive member 600. The lack of such a physical connection provides significant technical benefits to a user. For example, the user is no longer constrained by the presence of physical cords connecting to the elongated conductive member 600. Additionally, in the case of a guidewire system, for example, the user can feed medical devices, such as stents and catheters, over the wire 102 without having to remove or power down the wire 102. Such an ability allows the user to maintain uninterrupted sensor data from within the patient while placing the medical device onto the wire 102 and while placing the medical device within the human body.

Figure 9:
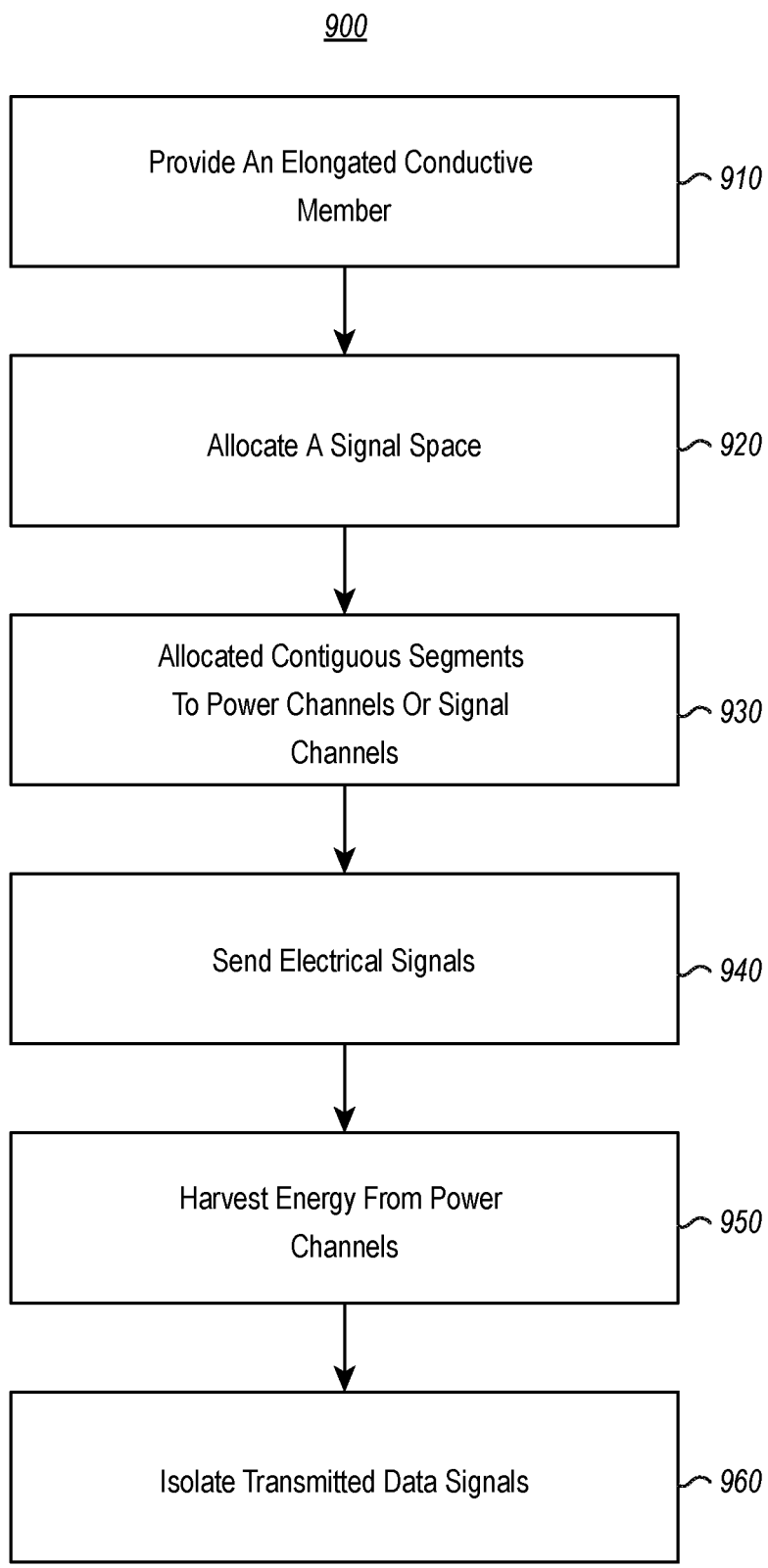
FIG. 9 illustrates a flow chart of a method for concurrent power and data transfer in a medical device.

FIG. 9 illustrates a flow chart of a method 900 for concurrent power and data transfer in a medical device. Method 900 includes an act 910 of providing an elongated conductive member. Act 910 comprises providing an elongated conductive member, at least a portion thereof configured for insertion within an intraluminal space, the elongated conductive member comprising a proximal portion and a distal portion configured to conduct electrical signals. For example, as depicted and described with respect FIGS. 1 and 2, the elongated conductive member may comprise a wire 102 within a guidewire system 100, a catheter 202 within a catheter system 200, or any other elongated conductive member suitable for insertion into an intraluminal space.

Method 900 also includes an act 920 of allocating a signal space. Act 920 comprises allocating a signal space into a plurality of unique contiguous segments. For example, as depicted and described with respect to FIG. 7, a signal space 700 may be segmented into time slots, frequency channels, or any other segmentation.

Additionally, method 900 includes an act 930 of allocating contiguous segments to power channels or signal channel. Act 930 comprises uniquely allocating each of the plurality of unique contiguous segments to one of (i) one or more power channels or (ii) one or more signal channels. For example, as depicted and described with respect to FIGS. 6A, 6B, and 7, the signal space may be segmented such that a one or more particular channels are used to provide power to the one or more sensors, while one or more other channels are used to receive data signals from the one or more sensors.

Method 900 includes an act 940 of sending electrical signals. Act 940 comprises sending the electrical signals, via the elongated conductive member, to one or more sensors that are in electrical connection with the elongated conductive member. For example, as depicted and described with respect to FIGS. 6A, 6B, and 8C, a power and data coupling device 630 can send electrical signals within power channels to the one or more sensors.

Further, method 900 includes an act 950 of harvesting energy from the power channels. Act 950 comprises harvesting energy from the electrical signals within at least one of the one or more power channels. For example, as depicted and described with respect to FIGS. 3, 6A, 6B, and 8C, the one or more sensors can utilize an energy harvester 132 to harvest power from the power channels and provide that power to the one or more sensors 121.

Further still, method 900 includes an act 960 of isolating transmitted data signals. Act 960 comprises isolating transmitted data signals from at least one of the one or more signal channels, the data signals transmitted via the elongated conductive member and the data signals generated by the one or more sensors. For example, as depicted and described with respect to 6A and 6B, the power and data coupling device 630 comprises filters that are configured to isolate the data signals from each other.

Aspects of the Invention

The invention is further specified in the following clauses:

Clause 1: A method for concurrent power and data transfer in a medical device, the method comprising:
providing an elongated conductive member, at least a portion thereof configured for insertion within an intraluminal space, the elongated conductive member comprising a proximal portion and a distal portion configured to conduct electrical signals;
allocating a signal space into a plurality of unique contiguous segments;
uniquely allocating each of the plurality of unique contiguous segments to one of (i) one or more power channels or (ii) one or more signal channels;
sending the electrical signals, via the elongated conductive member, to one or more sensors that are in electrical connection with the elongated conductive member;
harvesting energy from the electrical signals within at least one of the one or more power channels; and
isolating transmitted data signals from at least one of the one or more signal channels, the data signals transmitted via the elongated conductive member and the data signals generated by the one or more sensors.

Clause 2: The method as recited in any preceding clause, wherein both the proximal portion and the distal portion are conductive.

Clause 3: The method as recited in any preceding clause, wherein the elongated conductive member comprises a single conductive pathway extending from the proximal portion to the distal portion.

Clause 4: The method as recited in any preceding clause, wherein the elongated conductive member comprises multiple extensions that are removably attached to each other.

Clause 5: The method as recited in any preceding clause, wherein harvesting energy from at least one of the one or more power channels further comprises:
transmitting energy within the at least one of the one or more power channels, wherein the at least one of the one or more power channels comprises a particular unique contiguous segment of the signal space; and
providing power to all of the one or more sensors through the at least one of the one or more power channels, each sensor of the one or more sensors configured to receive power from the particular unique contiguous segment of the signal space.

Clause 6: The method as recited in any preceding clause, wherein harvesting energy from at least one of the one or more power channels further comprises:
transmitting energy within the at least one of the one or more power channels, wherein the at least one of the one or more power channels comprises a first unique contiguous segment of the signal space;
transmitting energy within a second power channel of the one or more power channels, wherein the second power channel of the one or more power channels comprises a second unique contiguous segment of the signal space;
providing power to a first subset of the one or more sensors through the at least one of the one or more power channels, each sensor of the first subset of the one or more sensors configured to receive energy from the first unique contiguous segment of the signal space; and
providing power to a second subset of the one or more sensors through the second power channel of the one or more power channels, each sensor of second subset of the one or more sensors configured to receive energy from the second unique contiguous segment of the signal space.

Clause 7: The method as recited in any preceding clause, wherein:
allocating the signal space into the plurality of unique contiguous segments comprises:
designating a plurality of unique contiguous time slots; and
uniquely allocating each of the plurality of unique contiguous segments to one of (i) the one or more power channels or (ii) the one or more signal channels, comprises:
uniquely allocating each of the plurality of unique contiguous time slots to one of (i) the one or more power channels or (ii) the one or more signal channels.

Clause 8: The method as recited in any preceding clause, wherein:
allocating the signal space into the plurality of unique contiguous segments comprises:
designating a plurality of unique contiguous regions of frequency; and
uniquely allocating each of the plurality of unique contiguous segments to one of (i) the one or more power channels or (ii) the one or more signal channels, comprises:
uniquely allocating each of the plurality of unique contiguous regions of frequency to one of (i) the one or more power channels or (ii) the one or more signal channels.

Clause 9: The method as recited in any preceding clause, wherein isolating transmitted data signals from at least one of the one or more signal channels comprises:

isolating multiple transmitted data signals in parallel, each data signal from the multiple data signals being associated with a different unique contiguous region of frequency selected from the plurality of unique contiguous regions of frequency.

Clause 10: The method as recited in any preceding clause, wherein the one or more sensors comprise at least a first sensor of a first type and a second sensor of a second, different type.

Clause 11: The method as recited in any preceding clause, wherein sending power, via the elongated conductive member, to the one or more sensors that are in electrical connection with the elongated conductive member comprises sending AC power.

Clause 12: A medical device system for concurrent power and data transfer, the medical device system comprising:
an elongated conductive member, at least a portion thereof configured for insertion within an intraluminal space, the elongated conductive member comprising a proximal portion and a distal portion;
one or more sensors that are in electrical connection with the elongated conductive member; and
one or more electrical components that are physically configured such that when activated, the one or more electrical components cause the medical device system to perform at least the following:
allocate a signal space into a plurality of unique contiguous segments,
uniquely allocate each of the plurality of unique contiguous segments to one of (i) one or more power channels or (ii) one or more signal channels,
send the electrical signals, via the elongated conductive member, to one or more sensors that are in electrical connection with the elongated conductive member;
harvest energy from the electrical signals within at least one of the one or more power channels, and
isolate transmitted data signals within at least one of the one or more signal channels, via the elongated conductive member, the data signals generated by the one or more sensors.

Clause 13: The medical device system as recited in any preceding clause, wherein both the proximal portion and the distal portion are conductive.

Clause 14: The medical device system as recited in any preceding clause, wherein the elongated conductive member comprises a single conductive pathway extending from the proximal portion to the distal portion.

Clause 15: The medical device system as recited in any preceding clause, wherein the elongated conductive member comprises multiple extensions that are removably attached to each other.

Clause 16: The medical device system as recited in any preceding clause, wherein harvesting energy from at least one of the one or more power channels further comprises:
transmitting energy within the at least one of the one or more power channels, wherein the at least one of the one or more power channels comprises a particular unique contiguous segment of the signal space; and
providing power to all of the one or more sensors through the at least one of the one or more power channels, each sensor of the one or more sensors receiving energy from the particular unique contiguous segment of the signal space.

Clause 17: The medical device system as recited in any preceding clause, wherein harvesting energy from at least one of the one or more power channels further comprises:
transmitting energy within the at least one of the one or more power channels, wherein the at least one of the one or more power channels comprises a first unique contiguous segment of the signal space;
transmitting energy within a second power channel of the one or more power channels, wherein the second power channel of the one or more power channels comprises a second unique contiguous segment of the signal space;
providing energy to a first subset of the one or more sensors through the at least one of the one or more power channel, each sensor of the first subset of the one or more sensors configured to receive energy from the first unique contiguous segment of the signal space; and
providing energy to a second subset of the one or more sensors through the second power channel of the one or more power channels, each sensor of second subset of the one or more sensors configured to receive energy from the second unique contiguous segment of the signal space.

Clause 18: The medical device system as recited in any preceding clause, wherein:
allocating the signal space into the plurality of unique contiguous segments comprises:
designating a plurality of unique contiguous time slots; and
uniquely allocating each of the plurality of unique contiguous segments to one of (i) the one or more power channels or (ii) the one or more signal channels, comprises:
uniquely allocating each of the plurality of unique contiguous time slots to one of (i) the one or more power channels or (ii) the one or more signal channels.

Clause 19: The medical device system as recited in any preceding clause, wherein:
allocating the signal space into the plurality of unique contiguous segments comprises:
designating a plurality of unique contiguous regions of frequency; and
uniquely allocating each of the plurality of unique contiguous segments to one of (i) the one or more power channels or (ii) the one or more signal channels, comprises:
uniquely allocating each of the plurality of unique contiguous regions of frequency to one of (i) the one or more power channels or (ii) the one or more signal channels.

Clause 20: The medical device system as recited in any preceding clause, wherein isolating transmitted data signals from at least one of the one or more signal channels comprises:
isolating multiple transmitted data signals in parallel, each data signal from the multiple data signals being associated with a different unique contiguous region of frequency selected from the plurality of unique contiguous regions of frequency.

Clause 21: The medical device system as recited in any preceding clause, wherein the one or more sensors are in electrical connection with the elongated conductive member through a substrate, the substrate comprising electrical pathways connecting individual components within the one or more sensors.

Clause 22: The medical device system as recited in any preceding clause, wherein the elongated conductive member comprises a first conductive pathway for use as a power channel and a second conductive pathway for user as a signal channel, both the first conductive pathway and the second conductive pathway extending from the proximal portion to the distal portion.

Clause 23: A computer-readable media comprising one or more physical computer-readable storage media having stored thereon computer-executable instructions that, when executed at one or more processors, cause a computer system to perform a method for concurrent power and data transfer in a single-member medical device, the method comprising:

providing an elongated conductive member, at least a portion thereof configured for insertion within an intraluminal space, the elongated conductive member comprising a proximal portion and a distal portion configured to conduct electrical signals;

allocating a signal space into a plurality of unique contiguous segments, uniquely allocating each of the plurality of unique contiguous segments to one of (i) one or more power channels or (ii) one or more signal channels, sending the electrical signals, via the elongated conductive member, to one or more sensors that are in electrical connection with the elongated conductive member;

harvesting energy from the electrical signals within at least one of the one or more power channels, and isolating transmitted data signals within at least one of the one or more signal channels, via the elongated conductive member, the data signals generated by the one or more sensors.

Conclusion

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, or less than 1% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may include properties, features (e.g., ingredients, components, members, elements, parts, and/or portions) described in other embodiments described herein. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

Further, the methods may be practiced by a computer system including one or more processors and computer-readable media such as computer memory. In particular, the computer memory may store computer-executable instructions that when executed by one or more processors cause various functions to be performed, such as the acts recited in the embodiments.

Computing system functionality can be enhanced by a computing systems' ability to be interconnected to other computing systems via network connections. Network connections may include, but are not limited to, connections via wired or wireless Ethernet, cellular connections, or even computer to computer connections through serial, parallel, USB, or other connections. The connections allow a computing system to access services at other computing systems and to quickly and efficiently receive application data from other computing systems.

Interconnection of computing systems has facilitated distributed computing systems, such as so-called "cloud" computing systems. In this description, "cloud computing" may be systems or resources for enabling ubiquitous, convenient, on-demand network access to a shared pool of configurable computing resources (e.g., networks, servers, storage, applications, services, etc.) that can be provisioned and released with reduced management effort or service provider interaction. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

Cloud and remote based service applications are prevalent. Such applications are hosted on public and private remote systems such as clouds and usually offer a set of web-based services for communicating back and forth with clients.

Many computers are intended to be used by direct user interaction with the computer. As such, computers have input hardware and software user interfaces to facilitate user interaction. For example, a modern general-purpose computer may include a keyboard, mouse, touchpad, camera, etc. for allowing a user to input data into the computer. In addition, various software user interfaces may be available.

Examples of software user interfaces include graphical user interfaces, text command line-based user interface, function key or hot key user interfaces, and the like.

Disclosed embodiments may comprise or utilize a special purpose or general-purpose computer including computer hardware, as discussed in greater detail below. Disclosed embodiments also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media and transmission computer-readable media.

Physical computer-readable storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry program code in the form of computer-executable instructions or data structures, and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for concurrent power and data transfer in a medical device, the method comprising:
   providing an elongated electrically conductive member, at least a portion thereof configured for insertion within an intraluminal space, the elongated electrically conductive member comprising a proximal portion and a distal portion configured to conduct electrical signals;
   allocating a signal space into a plurality of unique contiguous segments;
   uniquely allocating each of the plurality of unique contiguous segments to one of (i) one or more power channels or (ii) one or more signal channels;
   sending the electrical signals, via the elongated electrically conductive member, to one or more sensors that are in electrical connection with the elongated electrically conductive member;
   harvesting energy from the electrical signals within at least one of the one or more power channels; and
   isolating transmitted data signals from at least one of the one or more signal channels, the data signals transmitted via the elongated electrically conductive member and the data signals generated by the one or more sensors.

2. The method as recited in claim 1, wherein both the proximal portion and the distal portion are conductive.

3. The method as recited in claim 1, wherein the elongated electrically conductive member comprises a single conductive pathway extending from the proximal portion to the distal portion.

4. The method as recited in claim 3, wherein the elongated electrically conductive member comprises multiple extensions that are removably attached to each other.

5. The method as recited in claim 1, wherein harvesting energy from at least one of the one or more power channels further comprises:
   transmitting energy within the at least one of the one or more power channels, wherein the at least one of the one or more power channels comprises a particular unique contiguous segment of the signal space; and
   providing power to all of the one or more sensors through the at least one of the one or more power channels, each sensor of the one or more sensors configured to receive power from the particular unique contiguous segment of the signal space.

6. The method as recited in claim 1, wherein harvesting energy from at least one of the one or more power channels further comprises:
   transmitting energy within the at least one of the one or more power channels, wherein the at least one of the one or more power channels comprises a first unique contiguous segment of the signal space;

transmitting energy within a second power channel of the one or more power channels, wherein the second power channel of the one or more power channels comprises a second unique contiguous segment of the signal space;

providing power to a first subset of the one or more sensors through the at least one of the one or more power channels, each sensor of the first subset of the one or more sensors configured to receive energy from the first unique contiguous segment of the signal space; and providing power to a second subset of the one or more sensors through the second power channel of the one or more power channels, each sensor of second subset of the one or more sensors configured to receive energy from the second unique contiguous segment of the signal space.

7. The method as recited in claim 1, wherein:
allocating the signal space into the plurality of unique contiguous segments comprises:
designating a plurality of unique contiguous time slots; and
uniquely allocating each of the plurality of unique contiguous segments to one of (i) the one or more power channels or (ii) the one or more signal channels, comprises:
uniquely allocating each of the plurality of unique contiguous time slots to one of (i) the one or more power channels or (ii) the one or more signal channels.

8. The method as recited in claim 1, wherein:
allocating the signal space into the plurality of unique contiguous segments comprises:
designating a plurality of unique contiguous regions of frequency; and
uniquely allocating each of the plurality of unique contiguous segments to one of (i) the one or more power channels or (ii) the one or more signal channels, comprises:
uniquely allocating each of the plurality of unique contiguous regions of frequency to one of (i) the one or more power channels or (ii) the one or more signal channels.

9. The method as recited in claim 8, wherein isolating transmitted data signals from at least one of the one or more signal channels comprises:
isolating multiple transmitted data signals in parallel, each data signal from the multiple data signals being associated with a different unique contiguous region of frequency selected from the plurality of unique contiguous regions of frequency.

10. The method as recited in claim 1, wherein the one or more sensors comprise at least a first sensor of a first type and a second sensor of a second, different type.

11. The method as recited in claim 1, wherein sending power, via the elongated electrically conductive member, to the one or more sensors that are in electrical connection with the elongated electrically conductive member comprises sending AC power.

12. A medical device system for concurrent power and data transfer, the medical device system comprising:
an elongated electrically conductive member, at least a portion thereof configured for insertion within an intraluminal space, the elongated electrically conductive member comprising a proximal portion and a distal portion;

one or more sensors that are in electrical connection with the elongated electrically conductive member; and one or more electrical components that are physically configured such that when activated, the one or more electrical components cause the medical device system to perform at least the following:
allocate a signal space into a plurality of unique contiguous segments,
uniquely allocate each of the plurality of unique contiguous segments to one of (i) one or more power channels or (ii) one or more signal channels,
send electrical signals, via the elongated electrically conductive member, to one or more sensors that are in electrical connection with the elongated electrically conductive member,
harvest energy from the electrical signals within at least one of the one or more power channels, and
isolate transmitted data signals within at least one of the one or more signal channels, via the elongated electrically conductive member, the data signals generated by the one or more sensors.

13. The medical device system as recited in claim 12, wherein both the proximal portion and the distal portion are conductive.

14. The medical device system as recited in claim 12, wherein the elongated electrically conductive member comprises a single conductive pathway extending from the proximal portion to the distal portion.

15. The medical device system as recited in claim 14, wherein the elongated electrically conductive member comprises multiple extensions that are removably attached to each other.

16. The medical device system as recited in claim 12, wherein harvesting energy from at least one of the one or more power channels further comprises:
transmitting energy within the at least one of the one or more power channels, wherein the at least one of the one or more power channels comprises a particular unique contiguous segment of the signal space; and
providing power to all of the one or more sensors through the at least one of the one or more power channels, each sensor of the one or more sensors receiving energy from the particular unique contiguous segment of the signal space.

17. The medical device system as recited in claim 12, wherein harvesting energy from at least one of the one or more power channels further comprises:
transmitting energy within the at least one of the one or more power channels, wherein the at least one of the one or more power channels comprises a first unique contiguous segment of the signal space;
transmitting energy within a second power channel of the one or more power channels, wherein the second power channel of the one or more power channels comprises a second unique contiguous segment of the signal space;
providing energy to a first subset of the one or more sensors through the at least one of the one or more power channels, each sensor of the first subset of the one or more sensors configured to receive energy from the first unique contiguous segment of the signal space; and
providing energy to a second subset of the one or more sensors through the second power channel of the one or more power channels, each sensor of second subset of the one or more sensors configured to receive energy from the second unique contiguous segment of the signal space.

18. The medical device system as recited in claim 12, wherein:
allocating the signal space into the plurality of unique contiguous segments comprises:
designating a plurality of unique contiguous time slots; and
uniquely allocating each of the plurality of unique contiguous segments to one of (i) the one or more power channels or (ii) the one or more signal channels, comprises:
uniquely allocating each of the plurality of unique contiguous time slots to one of (i) the one or more power channels or (ii) the one or more signal channels.

19. The medical device system as recited in claim 12, wherein:
allocating the signal space into the plurality of unique contiguous segments comprises:
designating a plurality of unique contiguous regions of frequency; and
uniquely allocating each of the plurality of unique contiguous segments to one of (i) the one or more power channels or (ii) the one or more signal channels, comprises:
uniquely allocating each of the plurality of unique contiguous regions of frequency to one of (i) the one or more power channels or (ii) the one or more signal channels.

20. The medical device system as recited in claim 19, wherein isolating transmitted data signals from at least one of the one or more signal channels comprises:
isolating multiple transmitted data signals in parallel, each data signal from the multiple transmitted data signals being associated with a different unique contiguous region of frequency selected from the plurality of unique contiguous regions of frequency.

21. The medical device system as recited in claim 12, wherein the one or more sensors are in electrical connection with the elongated electrically conductive member through a substrate, the substrate comprising electrical pathways connecting individual components within the one or more sensors.

22. A computer-readable media comprising one or more physical computer-readable storage media having stored thereon computer-executable instructions that, when executed at one or more processors, cause a computer system to perform a method for concurrent power and data transfer in a single-member medical device, the method comprising:

providing an elongated electrically conductive member, at least a portion thereof configured for insertion within an intraluminal space, the elongated electrically conductive member comprising a proximal portion and a distal portion configured to conduct electrical signals;
allocating a signal space into a plurality of unique contiguous segments,
uniquely allocating each of the plurality of unique contiguous segments to one of (i) one or more power channels or (ii) one or more signal channels,
sending the electrical signals, via the elongated electrically conductive member, to one or more sensors that are in electrical connection with the elongated electrically conductive member;
harvesting energy from the electrical signals within at least one of the one or more power channels, and
isolating transmitted data signals within at least one of the one or more signal channels, via the elongated electrically conductive member, the transmitted data signals generated by the one or more sensors.

23. A method for concurrent power and data transfer in a medical device, the method comprising:
providing an elongated conductive member, at least a portion thereof configured for insertion within an intraluminal space, the elongated conductive member comprising a proximal portion and a distal portion configured to conduct electrical signals, wherein the elongated conductive member comprises a single electrically conductive pathway extending from the proximal portion to the distal portion;
allocating a signal space into a plurality of unique contiguous segments;
uniquely allocating each of the plurality of unique contiguous segments to one of (i) one or more power channels or (ii) one or more signal channels;
sending the electrical signals, via the elongated conductive member, to one or more sensors that are in electrical connection with the elongated conductive member;
harvesting energy from the electrical signals within at least one of the one or more power channels; and
isolating transmitted data signals from at least one of the one or more signal channels, the data signals transmitted via the elongated conductive member and the data signals generated by the one or more sensors.

24. The method as recited in claim 23, wherein the elongated conductive member comprises an electrically conductive guidewire.

* * * * *